(12) United States Patent
Brass et al.

(10) Patent No.: US 9,279,128 B2
(45) Date of Patent: Mar. 8, 2016

(54) RHAMNOSE PROMOTER EXPRESSION SYSTEM

(75) Inventors: Johann Brass, Ausserberg (CH); Christoph Kiziak, Visp (CH); Joachim Klein, Visp (CH); Ralf Ostendorp, Munich (DE)

(73) Assignee: LONZA AG, Basel (CH)

( * ) Notice: Subject to any disclaimer, the term of this patent is extended or adjusted under 35 U.S.C. 154(b) by 0 days.

(21) Appl. No.: 13/317,293

(22) Filed: Oct. 14, 2011

(65) Prior Publication Data

US 2012/0135463 A1 May 31, 2012

Related U.S. Application Data

(63) Continuation of application No. 11/791,989, filed as application No. PCT/EP2005/013013 on Dec. 5, 2005, now abandoned.

(30) Foreign Application Priority Data

Dec. 7, 2004 (EP) ..................................... 04028917

(51) Int. Cl.
*C12N 15/10* (2006.01)
*C12N 15/00* (2006.01)
*C12N 15/70* (2006.01)
*C07H 21/02* (2006.01)
*C12N 15/63* (2006.01)
*C12N 15/78* (2006.01)

(52) U.S. Cl.
CPC ................ *C12N 15/63* (2013.01); *C12N 15/78* (2013.01)

(58) Field of Classification Search
None
See application file for complete search history.

(56) References Cited

U.S. PATENT DOCUMENTS 5,240,831 A * 8/1993 Barnes .......................... 435/69.1

FOREIGN PATENT DOCUMENTS

| WO | WO 03/068956 | * | 8/2003 |
| WO | WO 2004/050877 | * | 6/2004 |
| WO | WO 2004/063343 | * | 7/2004 |

OTHER PUBLICATIONS

Kipp et al., Int. Arch. Allergy Immunol. 1996; 110:348-353.*
Volff et al., Mol Microbiol. 1996:21, 1037-1047.*

* cited by examiner

*Primary Examiner* — Nancy T Vogel
(74) *Attorney, Agent, or Firm* — Hoffmann & Baron, LLP

(57) ABSTRACT

Vectors expressible in a host that is the rhaBAD promoter region of the L-rhamnose operon operably linked to a transcriptional unit that is:
 a) a nucleic acid sequence which is heterologous to the host, and
 b) a prokaryotic signal sequence operably linked to the nucleic acid sequence.
The prokaryotic signal sequence is selected from signal peptides of periplasmatic binding proteins for sugars, amino acids, vitamins and ions. The expression of the nucleic acid sequence is controlled by the promoter region. The vector is used for the regulated heterologous expression of a nucleic acid sequence in a prokaryotic host. This is an isolated and purified nucleic acid sequence expressible in a host is the promoter region of the L-rhamnose operon. There is a method for producing a polypeptide in a host using the vector.

11 Claims, 17 Drawing Sheets

SEQUENCE LISTING

<160> NUMBER OF SEQ ID NOS: 75

<210> SEQ ID NO 1
<211> LENGTH: 129
<212> TYPE: DNA
<213> ORGANISM: Escherichia coli

<400> SEQUENCE: 1

```
caccacaatt cagcaaattg tgaacatcat cacgttcatc tttccctggt tgccaatggc      60 ccatttcct gtcagtaacg agaaggtcgc gaattcaggc gctttttaga ctggtcgtaa      120
tgaacaatt                                                             129
```

```
<210> SEQ ID NO 2
<211> LENGTH: 13
<212> TYPE: DNA
<213> ORGANISM: Escherichia coli

<400> SEQUENCE: 2
aggagatata cat                                                         13
```

```
<210> SEQ ID NO 3
<211> LENGTH: 1616
<212> TYPE: DNA
<213> ORGANISM: Escherichia coli

<400> SEQUENCE: 3
atcgatcacc acaattcagc aaattgtgaa catcatcacg ttcatctttc cctggttgcc      60
aatggcccat ttcctgtca gtaacgagaa ggtcgcgaat tcaggcgctt tttagactgg      120
tcgtaatgaa caattcttaa gaaggagata tacatatgaa aaagacagct atcgcgattg      180
cagtggcact ggctggtttc gctaccgtag cgcaggccga tatcgaactg acccagccgc      240
cttcagtgag cgttgcacca ggtcagaccg cgcgtatctc gtgtagcggc gatgcgctgg      300
gcgataaata cgcgagctgg taccagcaga acccgggca ggcgccagtt ctggtgattt       360
atgatgattc tgaccgtccc tcaggcatcc cggaacgctt tagcggatcc aacagcggca      420
acaccgcgac cctgaccatt agcggcactc aggcggaaga cgaagcggat tattattgcc      480
agagctatga ctctcctcag gttgtgtttg gcggcggcac gaagttaacc gttcttggcc      540
agccgaaagc cgcaccgagt gtgacgctgt tccgccgag cagcgaagaa ttgcaggcga       600
acaaagcgac cctggtgtgc ctgattagcg acttttatcc gggagccgtg acagtggcct      660
ggaaggcaga tagcagcccc gtcaaggcgg agtggagac caccacaccc tccaaacaaa      720
gcaacaacaa gtacgcggcc agcagctatc tgagcctgac gcctgagcag tggaagtccc      780
acagaagcta cagctgccag gtcacgcatg aggggagcac cgtggaaaaa accgttgcgc      840
cgactgaggc ctgataagca tgcgtaggag aaaataaaat gaaacaaagc actattgcac      900
tggcactctt accgttgctc ttcaccctg ttaccaaagc ccaggtgcaa ttgaaagaaa       960
gcggcccggc cctggtgaaa ccgacccaaa ccctgacccctgacctgtacc tttccggat     1020 ttagcctgtc cacgtctggc gttggcgtgg gctggattcg ccagccgcct gggaaagccc     1080
tcgagtggct ggctctgatt gattgggatg atgataagta ttatagcacc agcctgaaaa     1140
cgcgtctgac cattagcaaa gatacttcga aaatcaggt ggtgctgact atgaccaaca      1200
tggacccggt ggatacggcc acctattatt gcgcgcgtta tcctgttact cagcgttctt     1260
atatggatgt ttggggccaa ggcacccctgg tgacggttag ctcagcgtcg accaaaggtc    1320
caagcgtgtt tccgctggct ccgagcagca aaagcaccag cggcggcacg ctgcccctgg    1380
gctgcctggt taaagattat ttcccggaac cagtcaccgt gagctggaac agcggggcgc    1440
tgaccagcgg cgtgcatacc tttccggcgg tgctgcaaag cagcggcctg tatagcctga    1500
gcagcgttgt gaccgtgccg agcagcagct taggcactca gacctatatt tgcaacgtga    1560
accataaacc gagcaacacc aaagtggata aaaaagtgga accgaaaagc tgataa        1616
```

```
<210> SEQ ID NO 4
<211> LENGTH: 1639
<212> TYPE: DNA
<213> ORGANISM: Escherichia coli

<400> SEQUENCE: 4
atcgatcacc acaattcagc aaattgtgaa catcatcacg ttcatctttc cctggttgcc      60
aatggcccat tttcctgtca gtaacgagaa ggtcgcgaat tcaggcgctt tttagactgg     120
tcgtaatgaa caattcttaa gaaggagata tacatatgat gattactctg cgcaaacttc     180
ctctggcggt tgccgtcgca gcgggcgtaa tgtctgctca ggcaatggct gatatcgaac     240
tgacccagcc gccttcagtg agcgttgcac caggtcagac cgcgcgtatc tcgtgtagcg     300
gcaatgcgct gggcgataaa tacgcgagct ggtaccagca gaatcccggg caggcgccag     360
ttctggtgat ttatgatgat tctgaccgtc cctcaggcat cccggaacgc tttagcggat     420
ccaacagcgg caacaccgcg accctgacca ttagcggcac tcaggcggaa gacgaagcgg     480
attattattg ccagagctat gactctcctc aggttgtgtt tggcggcggc acgaagttaa     540
ccgttcttgg ccagccgaaa gccgcaccga gtgtgacgct gtttccgccg agcagcgaag     600
aattgcaggc gaacaaagcg accctggtgt gcctgattag cgactttat ccgggagccg     660 tgacagtggc ctggaaggca gatagcagcc ccgtcaaggc gggagtggag accaccacac     720
cctccaaaca aagcaacaac aagtacgcgg ccagcagcta tctgagcctg acgcctgagc     780
agtggaagtc ccacagaagc tacagctgcc aggtcacgca tgaggggagc accgtggaaa     840
aaaccgttgc gccgactgag gcctgataac tgcaggagat atacatatga aaataaaaac     900
aggtgcacgc atcctcgcat tatccgcatt aacgacgatg atgtttttccg cctcggctct     960 cgcccaggtg caattgaaag aaagcggccc ggccctggtg aaaccgaccc aaaccctgac    1020
cctgacctgt acctttccg gatttagcct gtccacgtct ggcgttggcg tgggctggat    1080
tcgccagccg cctgggaaag ccctcgagtg gctggctctg attgattggg atgatgataa    1140
gtattatagc accagcctga aaacgcgtct gaccattagc aaagatactt cgaaaaatca    1200
ggtggtgctg actatgacca acatggaccc ggtggatacg gccacctatt attgcgcgcg    1260
ttatcctgtt actcagcgtt cttatatgga tgtttgggc caaggcaccc tggtgacggt    1320
tagctcagcg tcgaccaaag gtccaagcgt gcttccgctg gctccgagca gcaaaagcac    1380
cagcggcggc acggctgccc tgggctgcct ggttaaagat tatttcccgg aaccagtcac    1440
cgtgagctgg aacagcgggg cgctgaccag cggcgtgcat accttccgg cggtgctgca    1500 aagcagcggc ctgtatagcc tgagcagcgt tgtgaccgtg ccgagcagca gcttaggcac    1560
tcagacctat atttgcaacg tgaaccataa accgagcaac accaaagtgg ataaaaaagt    1620
ggaaccgaaa agctgataa                                                 1639

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaaatcgata aatgaaacgc atatttg                                          27

<210> SEQ ID NO 6
<211> LENGTH: 27
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aaacttaagt tgttatcaac ttgttat                                           27

<210> SEQ ID NO 7
<211> LENGTH: 154
<212> TYPE: DNA
<213> ORGANISM: Escherichia coli

<400> SEQUENCE: 7
aaaatcgata actgaaacgc atatttgcgg attagttcat gactttatct ctaacaaatt       60
gaaattaaac atttaatttt attaaggcaa ttgtggcaca ccccttgctt tgtctttatc      120
aacgcaaata acaagttgat aacaacttaa gttt                                  154

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaaatcgatg catcacgccc cgcacaa                                           27

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aaacttaagt caggatttat tgtttta                                           27

<210> SEQ ID NO 10
<211> LENGTH: 218
<212> TYPE: DNA
<213> ORGANISM: Escherichia coli

<400> SEQUENCE: 10
aaaatcgatg catcacgccc cgcacaagga agcggtagtc actgcccgat acggacttta       60
cataactcaa ctcattcccc tcgctatcct tttattcaaa ctttcaaatt aaaatattta      120
tctttcattt tgcgatcaaa ataacacttt taaatctttc aatctgatta gattaggttg      180
ccgtttggta ataaaacaat aaatcctgac ttaagttt                              218

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaaatcgatg actgcgagtg ggagcac                                           27
```

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaacttaagg gcttgcttga ataactt                                        27

<210> SEQ ID NO 13
<211> LENGTH: 161
<212> TYPE: DNA
<213> ORGANISM: Escherichia coli

<400> SEQUENCE: 13
aaaatcgata ctctgctttt caggtaattt attcccataa actcagattt actgctgctt    60
cacgcaggat ctgagtttat gggaatgctc aacctggaag ccggaggttt tctgcagatt   120
cgcctgccat gatgaagtta ttcaagcaag cccttaagtt t                       161

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aaacatatga aaagacagc tatc                                            24

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aaaaagcttt tatcagcttt tcggttc                                        27

<210> SEQ ID NO 16
<211> LENGTH: 26
<212> TYPE: PRT
<213> ORGANISM: Escherichia coli

<400> SEQUENCE: 16

Met Lys Lys Thr Ala Ile Ala Ile Ala Val Ala Leu Ala Gly Phe Ala
 1               5                  10                  15

Thr Val Ala Gln Ala Ala Pro Lys Asp Asn
            20                  25

<210> SEQ ID NO 17
<211> LENGTH: 26
<212> TYPE: PRT
<213> ORGANISM: Escherichia coli

<400> SEQUENCE: 17

Met Lys Lys Thr Ala Ile Ala Ile Ala Val Ala Leu Ala Gly Phe Ala
 1               5                  10                  15

Thr Val Ala Gln Ala Asp Ile Glu Leu Thr

<210> SEQ ID NO 18
<211> LENGTH: 26
<212> TYPE: PRT
<213> ORGANISM: Escherichia coli

<400> SEQUENCE: 18

Val Lys Gln Ser Thr Ile Ala Leu Ala Leu Leu Pro Leu Leu Phe Thr
1               5                   10                  15
Pro Val Thr Lys Ala Arg Thr Pro Glu Met
            20                  25

<210> SEQ ID NO 19
<211> LENGTH: 26
<212> TYPE: PRT
<213> ORGANISM: Escherichia coli

<400> SEQUENCE: 19

Met Lys Gln Ser Thr Ile Ala Leu Ala Leu Leu Pro Leu Leu Phe Thr
1               5                   10                  15
Pro Val Thr Lys Ala Gln Val Gln Leu Lys
            20                  25

<210> SEQ ID NO 20
<211> LENGTH: 27
<212> TYPE: PRT
<213> ORGANISM: Erwinia chrysanthemi

<400> SEQUENCE: 20

Met Lys Ser Leu Ile Thr Pro Ile Thr Ala Gly Leu Leu Leu Ala Leu
1               5                   10                  15
Ser Gln Pro Leu Leu Ala Ala Thr Asp Thr Gly
            20                  25

<210> SEQ ID NO 21
<211> LENGTH: 27
<212> TYPE: PRT
<213> ORGANISM: Erwinia chrysanthemi

<400> SEQUENCE: 21

Met Lys Ser Leu Ile Thr Pro Ile Thr Ala Gly Leu Leu Leu Ala Leu
1               5                   10                  15
Ser Gln Pro Leu Leu Ala Asp Ile Glu Leu Thr
            20                  25

<210> SEQ ID NO 22
<211> LENGTH: 27
<212> TYPE: PRT
<213> ORGANISM: Erwinia chrysanthemi

<400> SEQUENCE: 22

Met Lys Ser Leu Ile Thr Pro Ile Thr Ala Gly Leu Leu Leu Ala Leu
1               5                   10                  15
Ser Gln Pro Leu Leu Ala Gln Val Gln Leu Lys
            20                  25

<210> SEQ ID NO 23
<211> LENGTH: 27
<212> TYPE: PRT
<213> ORGANISM: Erwinia carotovora

<400> SEQUENCE: 23

Met Lys Tyr Leu Leu Pro Thr Ala Ala Ala Gly Leu Leu Leu Ala
1               5                   10                  15

Ala Gln Pro Ala Met Ala Ala Asn Thr Gly Gly
            20                  25

<210> SEQ ID NO 24
<211> LENGTH: 27
<212> TYPE: PRT
<213> ORGANISM: Erwinia carotovora

<400> SEQUENCE: 24

Met Lys Tyr Leu Leu Pro Thr Ala Ala Ala Gly Leu Leu Leu Ala
1               5                   10                  15

Ala Gln Pro Ala Met Ala Asp Ile Glu Leu Thr
            20                  25

<210> SEQ ID NO 25
<211> LENGTH: 27
<212> TYPE: PRT
<213> ORGANISM: Erwinia carotovora

<400> SEQUENCE: 25

Met Lys Tyr Leu Leu Pro Thr Ala Ala Ala Gly Leu Leu Leu Ala
1               5                   10                  15

Ala Gln Pro Ala Met Ala Gln Val Gln Leu Lys
            20                  25

<210> SEQ ID NO 26
<211> LENGTH: 31
<212> TYPE: PRT
<213> ORGANISM: Xanthomonas campestris

<400> SEQUENCE: 26

Met Lys Pro Lys Phe Ser Thr Ala Ala Ala Ser Leu Phe Val Gly
1               5                   10                  15

Ser Leu Leu Val Ile Gly Val Ala Ser Ala Asp Pro Ala Leu Glu
            20                  25                  30

<210> SEQ ID NO 27
<211> LENGTH: 31
<212> TYPE: PRT
<213> ORGANISM: Xanthomonas campestris

<400> SEQUENCE: 27

Met Lys Pro Lys Phe Ser Thr Ala Ala Ala Ser Leu Phe Val Gly
1               5                   10                  15

Ser Leu Leu Val Ile Gly Val Ala Ser Ala Asp Ile Glu Leu Thr
            20                  25                  30

<210> SEQ ID NO 28
<211> LENGTH: 31
<212> TYPE: PRT
<213> ORGANISM: Xanthomonas campestris

<400> SEQUENCE: 28

Met Lys Pro Lys Phe Ser Thr Ala Ala Ala Ser Leu Phe Val Gly
1               5                   10                  15

Ser Leu Leu Val Ile Gly Val Ala Ser Ala Gln Val Gln Leu Lys
            20                  25                  30

<210> SEQ ID NO 29

```
<211> LENGTH: 30
<212> TYPE: PRT
<213> ORGANISM: Escherichia coli

<400> SEQUENCE: 29

Met Met Ile Thr Leu Arg Lys Leu Pro Leu Ala Val Ala Val Ala Ala
 1               5                  10                  15

Gly Val Met Ser Ala Gln Ala Met Ala Val Asp Phe His Gly
            20                  25                  30

<210> SEQ ID NO 30
<211> LENGTH: 30
<212> TYPE: PRT
<213> ORGANISM: Escherichia coli

<400> SEQUENCE: 30

Met Met Ile Thr Leu Arg Lys Leu Pro Leu Ala Val Ala Val Ala Ala
 1               5                  10                  15

Gly Val Met Ser Ala Gln Ala Met Ala Asp Ile Glu Leu Thr
            20                  25                  30

<210> SEQ ID NO 31
<211> LENGTH: 30
<212> TYPE: PRT
<213> ORGANISM: Escherichia coli

<400> SEQUENCE: 31

Met Met Ile Thr Leu Arg Lys Leu Pro Leu Ala Val Ala Val Ala Ala
 1               5                  10                  15

Gly Val Met Ser Ala Gln Ala Met Ala Gln Val Gln Leu Lys
            20                  25                  30

<210> SEQ ID NO 32
<211> LENGTH: 31
<212> TYPE: PRT
<213> ORGANISM: Escherichia coli

<400> SEQUENCE: 32

Met Lys Ile Lys Thr Gly Ala Arg Ile Leu Ala Leu Ser Ala Leu Thr
 1               5                  10                  15

Thr Met Met Phe Ser Ala Ser Ala Leu Ala Lys Ile Glu Glu Gly
            20                  25                  30

<210> SEQ ID NO 33
<211> LENGTH: 31
<212> TYPE: PRT
<213> ORGANISM: Escherichia coli

<400> SEQUENCE: 33

Met Lys Ile Lys Thr Gly Ala Arg Ile Leu Ala Leu Ser Ala Leu Thr
 1               5                  10                  15

Thr Met Met Phe Ser Ala Ser Ala Leu Ala Asp Ile Glu Leu Thr
            20                  25                  30

<210> SEQ ID NO 34
<211> LENGTH: 31
<212> TYPE: PRT
<213> ORGANISM: Escherichia coli

<400> SEQUENCE: 34

Met Lys Ile Lys Thr Gly Ala Arg Ile Leu Ala Leu Ser Ala Leu Thr
 1               5                  10                  15
```

-continued

Thr Met Met Phe Ser Ala Ser Ala Leu Ala Gln Val Gln Leu Lys
                20                  25                  30

<210> SEQ ID NO 35
<211> LENGTH: 28
<212> TYPE: PRT
<213> ORGANISM: Escherichia coli

<400> SEQUENCE: 35

Met Ser Ile Gln His Phe Arg Val Ala Leu Ile Pro Phe Phe Ala Ala
  1               5                  10                  15

Phe Cys Leu Pro Val Phe Ala His Pro Glu Thr Leu
                20                  25

<210> SEQ ID NO 36
<211> LENGTH: 28
<212> TYPE: PRT
<213> ORGANISM: Escherichia coli

<400> SEQUENCE: 36

Met Ser Ile Gln His Phe Arg Val Ala Leu Ile Pro Phe Phe Ala Ala
  1               5                  10                  15

Phe Cys Leu Pro Val Phe Ala Asp Ile Glu Leu Thr
                20                  25

<210> SEQ ID NO 37
<211> LENGTH: 28
<212> TYPE: PRT
<213> ORGANISM: Escherichia coli

<400> SEQUENCE: 37

Met Ser Ile Gln His Phe Arg Val Ala Leu Ile Pro Phe Phe Ala Ala
  1               5                  10                  15

Phe Cys Leu Pro Val Phe Ala Gln Val Gln Leu Lys
                20                  25

<210> SEQ ID NO 38
<211> LENGTH: 31
<212> TYPE: PRT
<213> ORGANISM: Escherichia coli

<400> SEQUENCE: 38

Met Thr Asn Ile Thr Lys Arg Ser Leu Val Ala Ala Gly Val Leu Ala
  1               5                  10                  15

Ala Leu Met Ala Gly Asn Val Ala Leu Ala Ala Asp Val Pro Ala
                20                  25                  30

<210> SEQ ID NO 39
<211> LENGTH: 31
<212> TYPE: PRT
<213> ORGANISM: Escherichia coli

<400> SEQUENCE: 39

Met Thr Asn Ile Thr Lys Arg Ser Leu Val Ala Ala Gly Val Leu Ala
  1               5                  10                  15

Ala Leu Met Ala Gly Asn Val Ala Leu Ala Asp Ile Glu Leu Thr
                20                  25                  30

<210> SEQ ID NO 40
<211> LENGTH: 31
<212> TYPE: PRT
<213> ORGANISM: Escherichia coli

```
<400> SEQUENCE: 40

Met Thr Asn Ile Thr Lys Arg Ser Leu Val Ala Ala Gly Val Leu Ala
 1               5                  10                  15

Ala Leu Met Ala Gly Asn Val Ala Leu Ala Gln Val Gln Leu Lys
             20                  25                  30

<210> SEQ ID NO 41
<211> LENGTH: 35
<212> TYPE: PRT
<213> ORGANISM: Escherichia coli

<400> SEQUENCE: 41

Met Lys Ser Pro Ala Pro Ser Arg Pro Gln Lys Met Ala Leu Ile Pro
 1               5                  10                  15

Ala Cys Ile Phe Leu Cys Phe Ala Ala Leu Ser Val Gln Ala Glu Glu
             20                  25                  30

Thr Pro Val
         35

<210> SEQ ID NO 42
<211> LENGTH: 35
<212> TYPE: PRT
<213> ORGANISM: Escherichia coli

<400> SEQUENCE: 42

Met Lys Ser Pro Ala Pro Ser Arg Pro Gln Lys Met Ala Leu Ile Pro
 1               5                  10                  15

Ala Cys Ile Phe Leu Cys Phe Ala Ala Leu Ser Val Gln Ala Asp Ile
             20                  25                  30

Glu Leu Thr
         35

<210> SEQ ID NO 43
<211> LENGTH: 35
<212> TYPE: PRT
<213> ORGANISM: Escherichia coli

<400> SEQUENCE: 43

Met Lys Ser Pro Ala Pro Ser Arg Pro Gln Lys Met Ala Leu Ile Pro
 1               5                  10                  15

Ala Cys Ile Phe Leu Cys Phe Ala Ala Leu Ser Val Gln Ala Gln Val
             20                  25                  30

Gln Leu Lys
         35

<210> SEQ ID NO 44
<211> LENGTH: 27
<212> TYPE: PRT
<213> ORGANISM: Escherichia coli

<400> SEQUENCE: 44

Met Lys His Ser Val Ser Val Thr Cys Cys Ala Leu Leu Val Ser Ser
 1               5                  10                  15

Ile Ser Leu Ser Tyr Ala Ala Glu Val Pro Ser
             20                  25

<210> SEQ ID NO 45
<211> LENGTH: 27
<212> TYPE: PRT
<213> ORGANISM: Escherichia coli
```

```
<400> SEQUENCE: 45

Met Lys His Ser Val Ser Val Thr Cys Cys Ala Leu Leu Val Ser Ser
1               5                   10                  15

Ile Ser Leu Ser Tyr Ala Asp Ile Glu Leu Thr
            20                  25

<210> SEQ ID NO 46
<211> LENGTH: 27
<212> TYPE: PRT
<213> ORGANISM: Escherichia coli

<400> SEQUENCE: 46

Met Lys His Ser Val Ser Val Thr Cys Cys Ala Leu Leu Val Ser Ser
1               5                   10                  15

Ile Ser Leu Ser Tyr Ala Gln Val Gln Leu Lys
            20                  25

<210> SEQ ID NO 47
<211> LENGTH: 25
<212> TYPE: PRT
<213> ORGANISM: Escherichia coli

<400> SEQUENCE: 47

Met Lys Trp Leu Cys Ser Val Gly Ile Ala Val Ser Leu Ala Leu Gln
1               5                   10                  15

Pro Ala Leu Ala Asp Asp Leu Phe Gly
            20                  25

<210> SEQ ID NO 48
<211> LENGTH: 24
<212> TYPE: PRT
<213> ORGANISM: Escherichia coli

<400> SEQUENCE: 48

Met Lys Trp Leu Cys Ser Val Gly Ile Ala Val Ser Leu Ala Leu Gln
1               5                   10                  15

Pro Ala Leu Asp Ile Glu Leu Thr
            20

<210> SEQ ID NO 49
<211> LENGTH: 25
<212> TYPE: PRT
<213> ORGANISM: Escherichia coli

<400> SEQUENCE: 49

Met Lys Trp Leu Cys Ser Val Gly Ile Ala Val Ser Leu Ala Leu Gln
1               5                   10                  15

Pro Ala Leu Ala Gln Val Gln Leu Lys
            20                  25

<210> SEQ ID NO 50
<211> LENGTH: 27
<212> TYPE: PRT
<213> ORGANISM: Escherichia coli

<400> SEQUENCE: 50

Met Lys Lys Ser Ile Leu Ala Leu Ser Leu Leu Val Gly Leu Ser Thr
1               5                   10                  15

Ala Ala Ser Ser Tyr Ala Ala Leu Pro Glu Thr
            20                  25
```

-continued

```
<210> SEQ ID NO 51
<211> LENGTH: 27
<212> TYPE: PRT
<213> ORGANISM: Escherichia coli

<400> SEQUENCE: 51

Met Lys Lys Ser Ile Leu Ala Leu Ser Leu Leu Val Gly Leu Ser Thr
 1               5                  10                  15

Ala Ala Ser Ser Tyr Ala Asp Ile Glu Leu Thr
            20                  25

<210> SEQ ID NO 52
<211> LENGTH: 27
<212> TYPE: PRT
<213> ORGANISM: Escherichia coli

<400> SEQUENCE: 52

Met Lys Lys Ser Ile Leu Ala Leu Ser Leu Leu Val Gly Leu Ser Thr
 1               5                  10                  15

Ala Ala Ser Ser Tyr Ala Gln Val Gln Leu Lys
            20                  25

<210> SEQ ID NO 53
<211> LENGTH: 22
<212> TYPE: PRT
<213> ORGANISM: Escherichia coli

<400> SEQUENCE: 53

Met Lys Leu Ala Ala Cys Phe Leu Thr Leu Leu Pro Gly Phe Ala Val
 1               5                  10                  15

Ala Ala Ser Trp Thr Ser
            20

<210> SEQ ID NO 54
<211> LENGTH: 22
<212> TYPE: PRT
<213> ORGANISM: Escherichia coli

<400> SEQUENCE: 54

Met Lys Leu Ala Ala Cys Phe Leu Thr Leu Leu Pro Gly Phe Ala Val
 1               5                  10                  15

Ala Asp Ile Glu Leu Thr
            20

<210> SEQ ID NO 55
<211> LENGTH: 22
<212> TYPE: PRT
<213> ORGANISM: Escherichia coli

<400> SEQUENCE: 55

Met Lys Leu Ala Ala Cys Phe Leu Thr Leu Leu Pro Gly Phe Ala Val
 1               5                  10                  15

Ala Gln Val Gln Leu Lys
            20

<210> SEQ ID NO 56
<211> LENGTH: 27
<212> TYPE: PRT
<213> ORGANISM: Escherichia coli

<400> SEQUENCE: 56

Met Lys Lys Leu Val Leu Ser Leu Ser Leu Val Leu Ala Phe Ser Ser
 1               5                  10                  15
```

Ala Thr Ala Ala Phe Ala Ala Ile Pro Gln Asn
            20                  25

<210> SEQ ID NO 57
<211> LENGTH: 27
<212> TYPE: PRT
<213> ORGANISM: Escherichia coli

<400> SEQUENCE: 57

Met Lys Lys Leu Val Leu Ser Leu Ser Leu Val Leu Ala Phe Ser Ser
1               5                   10                  15

Ala Thr Ala Ala Phe Ala Asp Ile Glu Leu Thr
            20                  25

<210> SEQ ID NO 58
<211> LENGTH: 27
<212> TYPE: PRT
<213> ORGANISM: Escherichia coli

<400> SEQUENCE: 58

Met Lys Lys Leu Val Leu Ser Leu Ser Leu Val Leu Ala Phe Ser Ser
1               5                   10                  15

Ala Thr Ala Ala Phe Ala Gln Val Gln Leu Lys
            20                  25

<210> SEQ ID NO 59
<211> LENGTH: 28
<212> TYPE: PRT
<213> ORGANISM: Escherichia coli

<400> SEQUENCE: 59

Met Lys Ile Lys Asn Ile Leu Leu Thr Leu Cys Thr Ser Leu Leu Leu
1               5                   10                  15

Thr Asn Val Ala Ala His Ala Lys Glu Val Lys Ile
            20                  25

<210> SEQ ID NO 60
<211> LENGTH: 28
<212> TYPE: PRT
<213> ORGANISM: Escherichia coli

<400> SEQUENCE: 60

Met Lys Ile Lys Asn Ile Leu Leu Thr Leu Cys Thr Ser Leu Leu Leu
1               5                   10                  15

Thr Asn Val Ala Ala His Ala Asp Ile Glu Leu Thr
            20                  25

<210> SEQ ID NO 61
<211> LENGTH: 28
<212> TYPE: PRT
<213> ORGANISM: Escherichia coli

<400> SEQUENCE: 61

Met Lys Ile Lys Asn Ile Leu Leu Thr Leu Cys Thr Ser Leu Leu Leu
1               5                   10                  15

Thr Asn Val Ala Ala His Ala Gln Val Gln Leu Lys
            20                  25

<210> SEQ ID NO 62
<211> LENGTH: 26
<212> TYPE: PRT
<213> ORGANISM: Escherichia coli

<400> SEQUENCE: 62

Met Leu Ala Phe Ile Arg Phe Leu Phe Ala Gly Leu Leu Leu Val Ile
1               5                   10                  15

Ser His Ala Phe Ala Ala Thr Val Gln Asp
            20                  25

<210> SEQ ID NO 63
<211> LENGTH: 26
<212> TYPE: PRT
<213> ORGANISM: Escherichia coli

<400> SEQUENCE: 63

Met Leu Ala Phe Ile Arg Phe Leu Phe Ala Gly Leu Leu Leu Val Ile
1               5                   10                  15

Ser His Ala Phe Ala Asp Ile Glu Leu Thr
            20                  25

<210> SEQ ID NO 64
<211> LENGTH: 26
<212> TYPE: PRT
<213> ORGANISM: Escherichia coli

<400> SEQUENCE: 64

Met Leu Ala Phe Ile Arg Phe Leu Phe Ala Gly Leu Leu Leu Val Ile
1               5                   10                  15

Ser His Ala Phe Ala Gln Val Gln Leu Lys
            20                  25

<210> SEQ ID NO 65
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gagggcaaaa aatg                                                      14

<210> SEQ ID NO 66
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
aggagaaaat aaaatg                                                    16

<210> SEQ ID NO 67
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
aggagatata catatg                                                    16

<210> SEQ ID NO 68
<211> LENGTH: 236

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Met Ile Thr Leu Arg Lys Leu Pro Leu Ala Val Ala Val Ala Ala
1               5                   10                  15

Gly Val Met Ser Ala Gln Ala Met Ala Asp Ile Glu Leu Thr Gln Pro
                20                  25                  30

Pro Ser Val Ser Val Ala Pro Gly Gln Thr Ala Arg Ile Ser Cys Ser
            35                  40                  45

Gly Asn Ala Leu Gly Asp Lys Tyr Ala Ser Trp Tyr Gln Gln Asn Pro
        50                  55                  60

Gly Gln Ala Pro Val Leu Val Ile Tyr Asp Asp Ser Asp Arg Pro Ser
65                  70                  75                  80

Gly Ile Pro Glu Arg Phe Ser Gly Ser Asn Ser Gly Asn Thr Ala Thr
                85                  90                  95

Leu Thr Ile Ser Gly Thr Gln Ala Glu Asp Glu Ala Asp Tyr Tyr Cys
                100                 105                 110

Gln Ser Tyr Asp Ser Pro Gln Val Val Phe Gly Gly Gly Thr Lys Leu
            115                 120                 125

Thr Val Leu Gly Gln Pro Lys Ala Ala Pro Ser Val Thr Leu Phe Pro
        130                 135                 140

Pro Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
        195                 200                 205

Gln Trp Lys Ser His Arg Ser Tyr Ser Cys Gln Val Thr His Glu Gly
    210                 215                 220

Ser Thr Val Glu Lys Thr Val Ala Pro Thr Glu Ala
225                 230                 235

<210> SEQ ID NO 69
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Met Lys Ile Lys Thr Gly Ala Arg Ile Leu Ala Leu Ser Ala Leu Thr
1               5                   10                  15

Thr Met Met Phe Ser Ala Ser Ala Leu Ala Gln Val Gln Leu Lys Glu
                20                  25                  30

Ser Gly Pro Ala Leu Val Lys Pro Thr Gln Thr Leu Thr Leu Thr Cys
            35                  40                  45

Thr Phe Ser Gly Phe Ser Leu Ser Thr Ser Gly Val Gly Val Gly Trp
        50                  55                  60

Ile Arg Gln Pro Pro Gly Lys Ala Leu Glu Trp Leu Ala Leu Ile Asp
65                  70                  75                  80
```

Trp Asp Asp Lys Tyr Tyr Ser Thr Ser Leu Lys Thr Arg Leu Thr
            85                  90                  95

Ile Ser Lys Asp Thr Ser Lys Asn Gln Val Val Leu Thr Met Thr Asn
        100                 105                 110

Met Asp Pro Val Asp Thr Ala Thr Tyr Tyr Cys Ala Arg Tyr Pro Val
    115                 120                 125

Thr Gln Arg Ser Tyr Met Asp Val Trp Gly Gln Gly Thr Leu Val Thr
130                 135                 140

Val Ser Ser Ala Ser Thr Lys Gly Pro Ser Val Leu Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
225                 230                 235                 240

Val Asp Lys Lys Val Glu Pro Lys Ser
                245

<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
aaacatatgg atatcgaact gacccag                                         27

<210> SEQ ID NO 71
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
aaactgcagt tatcaggcct cagtcgg                                         27

<210> SEQ ID NO 72
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
aaactgcagg agatatacat atgcaggtgc aattgaa                              37

<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence: Synthetic

```
                                    -continued
        primer

<400> SEQUENCE: 73
aaaaagcttt tatcagcttt tcggttc                                              27

<210> SEQ ID NO 74
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
aaacatatga aatacctatt gcctacggc                                            29

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
aaaaagctta ctacgaggag acgg                                                 24
```

RHAMNOSE PROMOTER EXPRESSION SYSTEM

This is a continuation of U.S. patent application Ser. No. 11/791,989, filed on May 31, 2007, that is a 371 national stage application of International Application PCT Patent Application PCT/EP2005/013013, filed on Dec. 5, 2005, that has benefit of European Patent Application EP 04028917.5, filed on Dec. 7, 2004.

The present invention concerns vectors for the heterologous expression of nucleic acids encoding e.g. polypeptides such as recombinant proteins in prokaryotic hosts. More specifically, the present invention relates to new vectors expressible in a host comprising the rhaBAD promoter region of the L-rhamnose operon operably linked to a transcriptional unit comprising
a) a nucleic acid sequence which is heterologous to said host
b) a prokaryotic signal sequence operably linked to said nucleic acid sequence, whereas said prokaryotic signal sequence is selected from signal peptides of periplasmatic binding proteins for sugars, amino acids, vitamins and ions and, whereas the expression of said nucleic acid sequence is controlled by said promoter region. Furthermore the invention relates to the use of these vectors for the heterologous expression of nucleic acids encoding e.g. polypeptides.

BACKGROUND OF THE INVENTION

Many systems have been described for the heterologous expression of nucleic acids encoding e.g. polypeptides such as recombinant proteins in prokaryotic systems. However, most heterologous gene expression systems in prokaryotic host systems have relied exclusively on a limited set of bacterial promoters. The most widely used prokaryotic promoters have included the lactose [lac] (Yanisch-Perron et al., 1985, Gene 33, 103-109), and the tryptophan [trp] (Goeddel et al., 1980, Nature (London) 287, 411-416) promoters, and the hybrid promoters derived from these two [tac and trc] (Brosius, 1984, Gene 27:161-172; Amann and Brosius, 1985, Gene 40, 183-190). Other inducible promoter systems such as the araB promoter inducible by arabinose (WO 86 04356), the rhamnose promoter rhaSB inducible by L-rhamnose (WO 03068956) or the rhamnose promoter rhaBAD inducible by L-rhamnose (WO 2004/050877) have been described as well for the heterologous expression of proteins. WO 2004/050877 describes the use of a rhaBAD promoter for the heterologous expression of nitrilase in $E.\ coli$. After induction with L-rhamnose, nitrilase activity in resting-cell assays could be obtained. However, in particular for the expression of complex polypeptides such as antibodies or antibody fragments it is advantageous to export the polypeptide from the cytoplasma to non-cytoplasmic locations (secretion) by using signal sequences, since the overproduction of heterologous proteins in the cytoplasm is often accompanied by the misfolding and segregation into insoluble aggregates (inclusion bodies). However, since the signal sequence can influence secondary and tertiary structure formation in the mature region of secretory polypeptides, the choice of the appropriate signal sequence in combination with an useful promoter is important for high production of functional polypeptides. Thus, there is a need to provide alternative prokaryotic expression systems for the heterologous expression of nucleic acid sequences.

SUMMARY OF THE INVENTION

These and other objects as will be apparent from the foregoing description have been achieved by providing new vectors, which are useful for high-level expression of a desired heterologous product, and which comprise the rhaBAD promoter region of the L-rhamnose operon, a heterologous nucleic acid sequence and a prokaryotic signal sequence selected from signal peptides of periplasmatic binding proteins for sugars, amino acids, vitamins and ions. In a first aspect, the object of the present invention is to provide a new vector expressible in a host comprising the rhaBAD promoter region of the L-rhamnose operon operably linked to a transcriptional unit comprising
a) a nucleic acid sequence which is heterologous to said host
b) a prokaryotic signal sequence operably linked to said nucleic acid sequence, whereas said prokaryotic signal sequence is selected from signal peptides of periplasmatic binding proteins for sugars, amino acids, vitamins and ions and, whereas the expression of said nucleic acid sequence is controlled by said promoter region. Also provided are: the use of said new vector for the regulated heterologous expression of a nucleic acid sequence in a prokaryotic host; an isolated and purified nucleic acid sequence expressible in a host comprising the rhaBAD promoter region of the L-rhamnose operon, a heterologous nucleotide sequence and a prokaryotic signal sequence selected from signal peptides of periplasmatic binding proteins for sugars, amino acids, vitamins and ions; a prokaryotic host transformed with said vector or said isolated and purified nucleic acid sequence; a method for producing a polypeptide in a host using said vector, and a vector comprising a promoter region, a heterologous nucleic acid sequence and a translation initiation region consisting of the sequence AGGAGATATACAT (SEQ ID NO: 2).

Other objects and advantages will become apparent to those skilled in the art from a review of the ensuing detailed description, which proceeds with reference to the following illustrative drawings, and the attendant claims.

DETAILED DESCRIPTION OF TEE INVENTION

Figure 1:
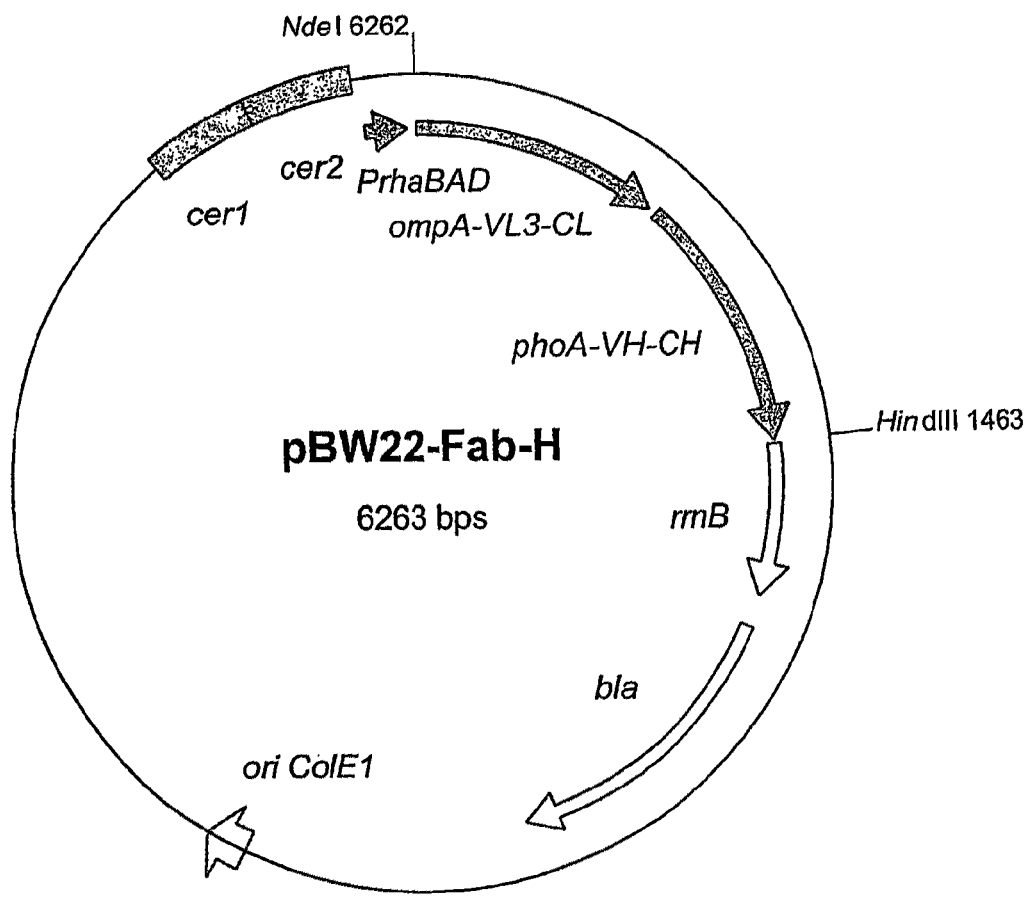
FIG. 1 shows plasmid pBW22-Fab-H containing the L-rhamnose inducible promoter (PrhaBAD), sequences coding for signal sequences operably linked to the light chain (ompA-VL3-CL) and the heavy chain (phoA-VH-CH) of a Fab fragment, and a transcription termination region (rrnB).

As used herein, the following definitions are supplied in order to facilitate the understanding of the present invention.

A "vector expressible in a host" or "expression vector" is a polynucleic acid construct, generated recombinantly or synthetically, with a series of specified polynucleic acid elements that permit transcription of a particular nucleic acid sequence in a host cell. Typically, this vector includes a transcriptional unit comprising a particular nucleic acid sequence to be transcribed operably linked to a promoter. A vector expressible in a host can be e.g. an autonomously or self-replicating plasmid, a cosmid, a phage, a virus or a retrovirus.

The terms "host", "host cell" and "recombinant host cell" are used interchangeably herein to indicate a prokaryotic cell into which one or more vectors or isolated and purified nucleic acid sequences of the invention have been introduced. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

The term "comprise" is generally used in the sense of include, that is to say permitting the presence of one or more features or components.

"Promoter" as used herein refers to a nucleic acid sequence that regulates expression of a transcriptional unit. A "promoter region" is a regulatory region capable of binding RNA polymerase in a cell and initiating transcription of a downstream (3′ direction) coding sequence. Within the promoter region will be found a transcription initiation site (conveniently defined by mapping with nuclease S1), as well as protein binding domains (consensus sequences) responsible for the binding of RNA polymerase such as the putative −35 region and the Pribnow box.

"L-rhamnose operon" refers to the rhaSR-rhaBAD operon as described for *E. coli* in Holcroft and Egan, 2000, J. Bacteriol. 182 (23), 6774-6782. The rhaBAD operon is a positively regulated catabolic operon which transcribes RhaB, RhaA and RhaD divergently from another rha operon, rhaSR, with approximately 240 bp of DNA separating their respective transcription start sites. The rhaSR operon encodes the two L-rhamnose-specific activators RhaS and RhaR. RhaR regulates transcription of rhaSR, whereas RhaS bind DNA upstream at −32 to −81 relative to the transcription start site of rhaBAD. Furthermore the rhaSR-rhaBAD intergenic operon contains CRP binding sites at positions −92,5 (CRP 1) relative to the transcription start site of rhaBAD and CRP binding sites at positions −92,5 (CRP 2), −115,5 (CRP 3) and 116,5 (CRP 4) relative to the transcription start site of rhaSR as well as a binding site for RhaR spanning −32 to −82 relative to the transcription start site of rhaSR.

With "rhaBAD promoter region of the L-rhamnose operon" is meant the rhaBAD operon consisting essentially of the rhaBAD transcription initiation site, the putative −35 region, the Pribnow box, the CRP binding site CPR1, the binding site for RhaS relative to the transcription start site of rhaBAD as well as CRP binding sites CRP 2-4, and binding site for RhaR relative to the transcription start site of rhaSR. With "rhaBAD promoter" is meant the promoter of the rhaBAD operon consisting essentially of the rhaBAD transcription initiation site, the putative −35 region, the Pribnow box, the binding site for RhaS and the CRP1 binding site region relative to the transcription start site of rhaBAD, and the CRP binding site CRP4 or a part thereof relative to the transcription start site of rhaSR.

"CRP" means "Catabolite regulator protein". "CRP" is often referred in the art as "cyclic AMP receptor protein", which has the synonymous meaning. CRP is a regulator protein controlled by cyclic AMP (cAMP) which mediates the activation of catabolic operons such as the L-rhamnose operon.

An "enhancer" is a nucleic acid sequence that acts to potentiate the transcription of a transcriptional unit independent of the identity of the transcriptional unit, the position of the sequence in relation to the transcriptional unit, or the orientation of the sequence. The vectors of the present invention optionally include enhancers.

"Transcriptional unit" as used herein refers to a nucleic acid sequence that is normally transcribed into a single RNA molecule. The transcriptional unit might contain one gene (monocistronic) or two (dicistronic) or more genes (polycistronic) that code for functionally related polypeptide molecules.

A nucleic acid sequence is "operably linked" when it is placed into a functional relationship with another nucleic acid sequence. For example, DNA for a signal sequence is operably linked to DNA for a protein if it is expressed as a preprotein that participates in the secretion of the protein; a promoter is operably linked to a coding sequence if it affects the transcription of the sequence; or a translation initiation region such as a ribosome binding site is operably linked to a nucleic acid sequence encoding e.g. a polypeptide if it is positioned so as to facilitate translation of the polypeptide. Linking can be accomplished by ligation at convenient restriction sites. If such sites do not exist, the synthetic oligonucleotide adaptors or linkers are used in accordance with conventional practice.

"Nucleic acid" or "nucleic acid sequence" or "isolated and purified nucleic acid or nucleic acid sequence" as referred in the present invention might be DNA, RNA, or DNA/RNA hybrid. In case the nucleic acid or the nucleic acid sequence is located on a vector it is usually DNA. DNA which is referred to herein can be any polydeoxynucleotide sequence, including, e.g. double-stranded DNA, single-stranded DNA, double-stranded DNA wherein one or both strands are composed of two or more fragments, double-stranded DNA wherein one or both strands have an uninterrupted phosphodiester backbone, DNA containing one or more single-stranded portion(s) and one or more double-stranded portion(s), double-stranded DNA wherein the DNA strands are fully complementary, double-stranded DNA wherein the DNA strands are only partially complementary, circular DNA, covalently-closed DNA, linear DNA, covalently cross-linked DNA, cDNA, chemically-synthesized DNA, semi-synthetic DNA, biosynthetic DNA, naturally-isolated DNA, enzyme-digested DNA, sheared DNA, labeled DNA, such as radiolabeled DNA and fluorochrome-labeled DNA, DNA containing one or more non-naturally occurring species of nucleic acid. DNA sequences can be synthesized by standard chemical techniques, for example, the phosphotriester method or via automated synthesis methods and PCR methods. The purified and isolated DNA sequence may also be produced by enzymatic techniques.

RNA which is referred to herein can be e.g. single-stranded RNA, cRNA, double-stranded RNA, double-stranded RNA wherein one or both strands are composed of two or more fragments, double-stranded RNA wherein one or both strands have an uninterrupted phosphodiester backbone, RNA containing one or more single-stranded portion(s) and one or more double-stranded portion(s), double-stranded RNA wherein the RNA strands are fully complementary, double-stranded RNA wherein the RNA strands are only partially complementary, covalently crosslinked RNA, enzyme-digested RNA, sheared RNA, mRNA, chemically-synthesized RNA, semi-synthetic RNA, biosynthetic RNA, naturally-isolated RNA, labeled RNA, such as radiolabeled RNA and fluorochrome-labeled RNA, RNA containing one or more non-naturally-occurring species of nucleic acid.

With "variants" or "variants of a sequence" is meant a nucleic acid sequence that vary from the reference sequence by conservative nucleic acid substitutions, whereby one or more nucleic acids are substituted by another with same characteristics. Variants encompass as well degenerated sequences, sequences with deletions and insertions, as long as such modified sequences exhibit the same function (functionally equivalent) as the reference sequence.

As used herein, the terms "polypeptide", "peptide", "protein", "polypeptidic" and "peptidic" are used interchangeably to designate a series of amino acid residues connected to the other by peptide bonds between the alpha-amino and carboxy groups of adjacent residues.

The term "isolated and purified nucleic acid sequence" refers to the state in which the nucleic acid sequence will be, in accordance with the present invention. The nucleic acid sequence will be free or substantially free of material with which they are naturally associated such as other nucleic acids with which they are found in their natural environment, or the environment in which they are prepared (e.g. cell culture) when such preparation is by recombinant technology practised in vitro or in vivo.

The terms "transformation", "transformed" or "introducing a nucleic acid into a host cell" denote any process wherein an extracellular nucleic acid like a vector, with or without accompanying material, enters a host cell. The term "cell transformed" or "transformed cell" means the cell or its progeny into which the extracellular nucleic acid has been introduced and thus harbours the extracellular nucleic acid. The nucleic acid might be introduced into the cell so that the nucleic acid is replicable either as a chromosomal integrant or as an extra chromosomal element. Transformation of appropriate host cells with e.g. an expression vector can be accomplished by well known methods such as microinjection, electroporation, particle bombardment or by chemical methods such as Calcium phosphate-mediated transformation, described e.g. in Maniatis et al. 1982, Molecular Cloning, A laboratory Manual, Cold Spring Harbor Laboratory or in Ausubel et al. 1994, Current protocols in molecular biology, John Wiley and Sons.

"Heterologous nucleic acid sequence" or "nucleic acid sequence heterologous to a host" means a nucleic acid sequence which encodes e.g. an expression product such as a polypeptide that is foreign to the host ("heterologous expression" or "heterologous product") i.e. a nucleic acid sequence originating from a donor different from the host or a chemically synthesized nucleic acid sequence which encodes e.g. an expression product such as a polypeptide that is foreign to the host. In case the host is a particular prokaryotic species, the heterologous nucleic acid sequence is preferably originated from a different genus or family, more preferred from a different order or class, in particular from a different phylum (division) and most particular from a different domain (empire) of organisms.

The heterologous nucleic acid sequence originating from a donor different from the host can be modified, before it is introduced into a host cell, by mutations, insertions, deletions or substitutions of single nucleic acids or a part of the heterologous nucleic acid sequence as long as such modified sequences exhibit the same function (functionally equivalent) as the reference sequence. A heterologous nucleic acid sequence as referred herein encompasses as well nucleic sequences originating from a different domain (empire) of organisms such as from eukaryotes (of eukaryotic origin) such as e.g. human antibodies which have been used in phage display libraries and of which single nucleic acids or a part of the nucleic acid sequences have been modified according to the "codon usage" of a prokaryotic host.

"Signal sequence" or "signal peptide sequence" refers to a nucleic acid sequence which encodes a short amino acid sequence (i.e., signal peptide) present at the NH2-terminus of certain proteins that are normally exported by cells to non-cytoplasmic locations (e.g., secretion) or to be membrane components. Signal peptides direct the transport of proteins from the cytoplasm to non-cytoplasmic locations.

"Translation initiation region" is a signal region which promotes translation initiation and which functions as the ribosome binding site such as the Shine Dalgarno sequence.

"Transcription termination region" refers to a sequence which causes RNA polymerase to terminate transcription. The transcription termination region is usually part of a transcriptional unit and increases the stability of the mRNA.

"Antibody" refers to a class of plasma proteins produced by the B-cells of the immune system after stimulation by an antigen. Mammal (i.e. Human) antibodies are immunoglobulins of the Ig G, M, A, E or D class. The term "antibody" as used for the purposes of this invention includes, but is not limited to, polyclonal antibodies, monoclonal antibodies, anti-idiotypic antibodies and auto-antibodies present in autoimmune diseases, such as diabetes, multiple sclerosis and rheumatoid arthritis as well as chimeric antibodies. The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids.

The term antibody is used to mean whole antibodies and binding fragments thereof. Binding fragments include single chain fragments, Fv fragments and Fab fragments.

The term "single-chain antibody" includes such non-natural antibody formats which combine only the antigen-binding regions of antibodies on a single stably-folded polypeptide chain. As such, single-chain antibodies are of considerably smaller size than classical immunoglobulins but retain the antigen-specific binding properties of antibodies. Single-chain antibodies are widely used for a variety of different applications, including for example as therapeutics, diagnostics, research tools etc.

The term Fab fragment is sometimes used in the art to mean the binding fragment resulting from papain cleavage of an intact antibody. The terms Fab' and F(ab')2 are sometimes used in the art to refer to binding fragments of intact antibodies generated by pepsin cleavage. In the context of the present invention, Fab is used to refer generically to double chain binding fragments of intact antibodies having at least substantially complete light and heavy chain variable domains sufficient for antigen-specific bindings, and parts of the light and heavy chain constant regions sufficient to maintain association of the light and heavy chains. An example of such Fab is described in Skerra et al., 1988, Science 240(4855), 1038-41, for instance. A Fab fragment e.g. of the IgG idiotype might or might not contain at least one of the two cysteine residues that form the two inter-chain disulfide bonds between the two heavy chains in the intact immunoglobulin. Usually, Fab fragments are formed by complexing a full-length or substantially full-length light chain with a heavy chain comprising the variable domain and at least the CH1 domain of the constant region. In addition, the C-terminal cysteine on the light chain may be replaced with serine or to another amino acid to eliminate the interchain disulfide bond between the heavy and light chains according to the present invention.

Further encompassed are chimeric antibodies which are antibodies whose light and heavy chain genes have been constructed, typically by genetic engineering, from immunoglobulin gene segments (e.g., segments encoding the variable region and segments encoding the constant region), for example, belonging to different species. For example, the variable (V) segments of the genes from a mouse monoclonal antibody can be joined to human constant (C) segments, such as IgG1 an IgG4. A typical chimeric antibody is thus a hybrid protein consisting of the V or antigen-binding domain from a mouse antibody and a C or effector domain from a human antibody. Chimeric antibodies have the same or similar binding specificity and affinity as a mouse or other nonhuman antibody that provides the variable regions of the antibody.

The term "human antibody" includes antibodies having variable and constant regions (if present) derived from human germline immunoglobulin sequences including either natural or artificial, engineered affinity maturation. Human antibodies of the invention can include amino acid residues not encoded by human germline immunoglobulin sequences (e.g., mutations introduced by random or site-specific mutagenesis in vitro or by somatic mutation in vivo). However, the term "human antibody" does include antibodies in which CDR sequences derived from the germline of another mammalian species, such as a mouse, have been grafted onto human framework sequences (i.e. humanized antibodies). Functional variants of such "human antibodies", e.g. truncated versions thereof or engineered muteins where e.g. individual proline or cysteine residues have been engineered by the means of genetic engineering well known in the art are encompassed by the term, in contrast. Examples of such may be found e.g. in WO 98/02462. However, the term only relates to the amino acid sequence of such antibody, irrespective of any glycosylation or other chemical modification of the peptide backbone.

In one aspect, the present invention provides a vector expressible in a host comprising the rhaBAD promoter region of the L-rhamnose operon operably linked to a transcriptional unit comprising
a) a nucleic acid sequence which is heterologous to said host
b) a prokaryotic signal sequence operably linked to said nucleic acid sequence, whereas said prokaryotic signal sequence is selected from signal peptides of periplasmatic binding proteins for sugars, amino acids, vitamins and ions and, whereas the expression of said nucleic acid sequence is controlled by said promoter region.

The vector according to the invention is preferably an autonomously or self-replicating plasmid, a cosmid, a phage, a virus or a retrovirus. A wide variety of host/vector combinations may be employed in expressing the nucleic acid sequences of this invention. Useful expression vectors, for example, may consist of segments of chromosomal, non-chromosomal and/or synthetic nucleic acid sequences. Suitable vectors include vectors with specific host range such as vectors specific for e.g. *E. coli* as well as vectors with broadhost-range such as vectors useful for Gram-negative bacteria. "Low-copy", "medium-copy" as well as "high copy" plasmids can be used.

Useful vectors for e.g. expression in *E. coli* are: pQE70, pQE60 and pQE-9 (QIAGEN, Inc.); pBluescript Vektoren, PhagescriptVektoren, pNH8A, pNH16a, pNH18A, pNH46A (Stratagene Cloning Systems, Inc.); ptrc99a, pKK223-3, pKK233-3, pDR540, pRIT5 (Pharmacia Bio-tech, Inc.); pLG338, pACYC184, pBR322, pUC18, pUC19, pKC30, pRep4, pACYC177, pACYC184, pRSF1010 and pBW22 (Wilms et al., 2001, Biotechnology and Bioengineering, 73 (2) 95-103) or derivates thereof such as plasmid pBW22-Fab-H or plasmid pAKL14. Further useful plasmids are well known to the person skilled in the art and are described e.g. in "Cloning Vectors" (Eds. Pouwels P. H. et al. Elsevier, Amsterdam-New York-Oxford, 1985).

Preferred vectors of the present inventions are autonomously or self-replicating plasmids, more preferred are vectors with specific host range such as vectors specific for e.g. *E. coli*. Most preferred are pBR322, pUC18, pACYC177, pACYC184, pRSF1010 and pBW22 or derivates thereof such as pBW22-Fab-H or pAKL14, in particular pBW22-Fab-H or pAKL14, most particular pAKL14.

In a preferred embodiment, the rhaBAD promoter region of the L-rhamnose operon is the rhaBAD promoter. In a particular preferred embodiment, the rhaBAD promoter consists of the sequence SEQ ID NO. 1, a sequence complementary thereof and variants thereof. Preferably the rhaBAD promoter region of the L-rhamnose operon, the rhaBAD promoter and the rhaBAD promoter consisting of the sequence SEQ ID NO. 1, a sequence complementary thereof and variants thereof are from the L-rhamnose operon of *E. coli*.

In another preferred embodiment of the invention the vector expressible in a prokaryotic host comprises apart from the rhaBAD promoter region of the L-rhamnose operon operably linked to a transcriptional unit furthermore sequences encoding the L-rhamnose-specific activators RhaS and RhaR including their respective native promoter sequences. Upon expression the RhaS and RhaR proteins control the activity of the rhaBAD promoter.

As prokaryotic signal sequence selected from signal peptides of periplasmatic binding proteins for sugars, amino acids, vitamins and ions, signal peptides such as PelB (*Erwinia chrysantemi*, Pectate lyase precursor), PelB (*Erwinia carotovora*, Pectate lyase precursor), PelB (*Xanthomonas campestris*, Pectate lyase precursor), LamB (*E. coli*, Maltoporin precursor), MalE (*E. coli*, Maltose-binding protein precursor), Bla (*E. coli*, Beta-lactamase), OppA (*E. coli*, Periplasmic oligopeptide-binding protein), TreA (*E. coli*, periplasmic trehalase precursor), MppA (*E. coli*, Periplasmic murein peptide-binding protein precursor), BglX (*E. coli*, Periplasmic beta-glucosidase precursor), ArgT (*E. coli*, Lysine-arginine-ornithine binding periplasmic protein precursor), MalS (*E. coli*, Alpha-amylase precursor), HisJ (*E. coli*, Histidine-binding periplasmic protein precursor), XylF (*E. coli*, D-Xylose-binding periplasmic protein precursor), FecB (*E. coli*, dicitrate-binding periplasmic protein precursor), OmpA (*E. coli*, outer membrane protein A precursor) and PhoA (*E. coli*, Alkaline phosphatase precursor) can be used.

In a preferred embodiment, the signal sequence is selected from the *E. coli* signal peptides LamB (Maltoporin precursor), MalE (Maltose-binding protein precursor), Bla (Beta-lactamase), OppA (Periplasmic oligopeptide-binding protein), TreA (periplasmic trehalase precursor), MppA (Periplasmic murein peptide-binding protein precursor), BglX (Periplasmic beta-glucosidase precursor), ArgT (Lysine-arginine-ornithine binding periplasmic protein precursor), MalS (Alpha-amylase precursor), HisJ (Histidine-binding periplasmic protein precursor), XylF (D-Xylose-binding periplasmic protein precursor), FecB (dicitrate-binding periplasmic protein precursor), OmpA (outer membrane protein A precursor) and PhoA (Alkaline phosphatase precursor). These are particularly useful for heterologous expression in *E. coli*. More preferred are the *E. coli* signal peptides LamB (Maltoporin precursor), MalE (Maltose-binding protein precursor), Bla (Beta-lactamase), TreA (periplasmic trehalase precursor), ArgT (Lysine-arginine-ornithine binding periplasmic protein precursor), FecB (dicitrate-binding periplasmic protein precursor). Most particular preferred are the *E. coli* signal peptides LamB (Maltoporin precursor) and MalE (Maltose-binding protein precursor). In case a dicistronic or polycistronic transcriptional unit is used, different or identical signal sequences operably linked to each of the cistrons can be applied. Preferably different signal sequences are used in such a case. The signal sequences to be employed in the expression vectors of the present invention can be obtained commercially or synthesized chemically. For example, signal sequences can be synthesized according to the solid phase phosphoramidite triester method described, e.g., in Beaucage & Caruthers, Tetrahedron Letts. 22:1859-1862 (1981), using an automated synthesizer, as described in Van Devanter et. al., Nucleic Acids Res. 12:6159-6168 (1984). Purification of oligonucleotides can be performed by either native acrylamide gel electrophoresis or by anion-exchange HPLC as described in Pearson & Reanier, J. Chrom. 255:137-149 (1983).

The transcriptional unit according to the present invention usually further comprises a translation initiation region upstream of the initiation point of the translation of said transcriptional unit, said translation initiation region consisting of the sequence AGGAGATATACAT (SEQ ID NO. 2), whereas said translation initiation region is operably linked to said nucleic acid sequence. The sequence AGGAGATATACAT (SEQ ID NO. 2) is usually located upstream directly adjacent to the initiation point of the translation of the transcriptional unit which can be ATG, GTG or TTG.

Usually, said transcriptional unit further comprises a transcription termination region selected from rrnB, RNA 1, T7Te, rrnB T1, trp a L126, trp a, tR2, T3Te, P14, tonB t, and trp a L153. Preferably, the rrnB transcriptional terminator sequence is used.

The heterologous nucleic acid sequence according to the present invention encodes an expression product that is foreign to the host. In case the host is a prokaryotic species such as *E. coli* the nucleic acid sequence of interest is more preferably from another class like the gammaproteobacteria such as from e.g. *Burkholderia* sp., in particular from a different phylum such as archae bacteria, and most particular from an eukaryotic organism such as mammals in particular from humans. However, the heterologous nucleic acid sequence might be modified according to the "codon usage" of the host. The heterologous sequence according to the present invention is usually a gene of interest. The gene of interest preferably encodes a heterologous polypeptide such as a structural, regulatory or therapeutic protein, or N- or C-terminal fusions of structural, regulatory or therapeutic protein with other proteins ("Tags") such as green fluorescent protein or other fusion proteins. The heterologous nucleic acid sequence might encode as well a transcript which can be used in the form of RNA, such as e.g. antisense-RNA.

The protein may be produced as an insoluble aggregate or as a soluble protein which is present in the cytoplasm or in the periplasmic space of the host cell, and/or in the extracellular medium. Preferably, the protein is produced as a soluble protein which is present in the periplasmic space of the host cell and/or in the extracellular medium. Examples of proteins include hormones such as growth hormone, growth factors such as epidermal growth factor, analgesic substances like enkephalin, enzymes like chymotrypsin, antibodies, receptors to hormones and includes as well proteins usually used as a visualizing marker e.g. green fluorescent protein.

Other proteins of interest are growth factor receptors (e.g., FGFR, PDGFR, EFG, NGFR, and VEGF) and their ligands. Other proteins are G-protein receptors and include substance K receptor, the angiotensin receptor, the [alpha]- and [beta]-adrenergic receptors, the serotonin receptors, and PAF receptor (see, e.g. Gilman, Ann. Rev. Biochem. 56, 625-649 (1987). Other proteins include ion channels (e.g., calcium, sodium, potassium channels), muscarinic receptors, acetylcholine receptors, GABA receptors, glutamate receptors, and dopamine receptors (see Harpold, U.S. Pat. Nos. 5,401,629 and 5,436,128). Other proteins of interest are adhesion proteins such as integrins, selecting, and immunoglobulin superfamily members (see Springer, Nature 346, 425-433 (1990). Osborn, Cell 62, 3 (1990); Hynes, Cell 69, 11 (1992)). Other proteins are cytokines, such as interleukins IL-1 through IL-13, tumor necrosis factors [alpha] and [beta], interferons [alpha], [beta], and [gamma], tumor growth factor Beta (TGF-[beta]), colony stimulating factor (CSF) and granulocyte monocyte colony stimulating factor (GM-CSF) (see Human Cytokines: Handbook for Basic & Clinical Research. Aggrawal et al. eds., Blackwell Scientific, Boston, Mass. 1991). Other proteins of interest are intracellular and intercellular messengers, such as, adenyl cyclase, guanyl cyclase, and phospholipase C. Drugs are also proteins of interest. The heterologous protein of interest can be of human, mammalian or prokaryotic origin. Other proteins are antigens, such as glycoproteins and carbohydrates to from microbial pathogens, both viral and bacterial, and tumors. Other proteins are enzymes like chymosin, proteases, polymerases, dehydrogenases, nucleases, glucanases, oxidases, α-amylase, oxidoreductases, lipases, amidases, nitril hydratases, esterases or nitrilases.

Preferably, the heterologous nucleic acid sequence, according to the present invention, encodes a polypeptide, more preferably an antibody and most preferably a Fab fragment. In particular a human antibody or a humanised antibody, more particularly a human Fab fragment is encoded by the nucleic acid sequence. The human Fab fragment encoded by the nucleic acid sequence is preferably either a human antibody fragment or a human antibody fragment that was grafted with at least one CDR from another mammalian species.

In one more preferred embodiment, the human Fab fragment is a fully human HuCAL-Fab as obtainable from an artificial, consensus-framework-based human antibody phage library that was artificially randomized in the CDR as described by Knappik et al., 2000, J. Mol. Biol. 296 (1), 57-86.

In another more preferred optional embodiment, the, optionally chimeric, CDR grafted, human Fab fragment is a non-HuCAL-Fab as opposed to the HuCAL-Fab definition in the foregoing, which in case of a fully human Fab fragment preferably means that it does not share the HuCAL consensus sequence framework but its non-CDR sequence portions are at least 70% more preferably 85%, most preferably 95% identical in amino acid sequence to the respective variable and constant light and heavy chains germline-encoded sequences, additionally and more preferably that its CDRs are directly obtained from naturally occurring genomic sequences of lymphoid cells including genomic affinity maturation events.

The Fab fragment is preferably derived from an IgG antibody and does not contain cysteine residues that form the two interchain disulfide bonds between the two heavy chains in the intact immunoglobulin. In particular, the heavy and the light chain of the antibody or preferably of the Fab fragment are encoded by a dicistronic transcriptional unit, whereas each chain is operably linked to a prokaryotic signal sequence selected from signal peptides of periplasmatic binding proteins for sugars, amino acids, vitamins and ions and an identical translation initiation region upstream of the initiation point of the translation of the transcriptional unit. Preferably, the translation initiation region consists of the sequence AGGAGATATACAT (SEQ ID NO. 2).

In the present invention, the order and the distance in which the signal sequence and the heterologous nucleic acid sequence are arranged within the expression vectors can be varied. In preferred embodiments, the signal sequence is 5' (upstream) to the nucleic acid sequence encoding e.g. the polypeptide of interest. The signal peptide sequence and the nucleic acid sequence encoding e.g. the polypeptide of interest can be separated by zero to about 1000 amino acids. In preferred embodiments, the signal peptide sequence and nucleic acid sequence encoding e.g. the polypeptide of interest are directly adjacent to each other, i.e. separated by zero nucleic acids.

Preferably, the rhaBAD promoter region and the operably linked transcriptional unit of the vector of the present invention consists of the sequence SEQ ID NO. 3, a sequence complementary thereof and variants thereof.

More preferably, the rhaBAD promoter region and the operably linked transcriptional unit of the vector of the present invention consist of the sequence SEQ ID NO. 4, a sequence complementary thereof and variants thereof.

Also encompassed by the present invention is the use of a vector according to the invention for the regulated heterologous expression of a nucleic acid sequence in a prokaryotic host. The expression can be regulated by the amount of L-rhamnose available to the prokaryotic host. Usually, the amount of L-rhamnose in the medium of the cultured prokaryotic host is between 0.01 and 100 g/l, preferably between 0.1 and 10 g/l, more preferably between 1 and 5 g/l.

Preferably, the heterologous nucleic acid sequence encodes for a polypeptide, more preferably for an antibody and most preferably for a Fab fragment, whereas the heavy and light chains of the antibody or the Fab fragment are expressed in equal amounts, thus leading to high concentrations of functional antibody or Fab fragment. In particular a human antibody or a humanised antibody more particular a human Fab fragment, most particular a human Fab fragment as described above is encoded by the heterologous nucleic acid sequence.

In order to obtain high concentrations of functional antibody or Fab fragment it is essential to have an equal amount of the heavy and light chains being expressed. In case one of both chains is overproduced compared to the other chain, non-reducible high molecular weight immunoreactive aggregates can be built, which is undesirably. It has been surprisingly found that with the vectors of the present invention high titers of functional antibodies can be obtained whereas only very low amounts of overproduced light or heavy chain or high molecular weight immunoreactive aggregates are built. Usually, less than 20%, preferably less than 10% of the expressed amount of antibody or Fab fragment are expressed as overproduced light or heavy chain or high molecular weight immunoreactive aggregates. The amount of the heavy and light chains overproduced and of high molecular weight immunoreactive aggregates can be measured by analysing extracts of the host expressing the antibody or the Fab fragment such as lysozyme extracts of the cultured host cell using SDS-PAGE or Western blot.

In still another aspect, the invention provides an isolated and purified nucleic acid sequence expressible in a host comprising the rhaBAD promoter region of the L-rhamnose operon operably linked to a transcriptional unit comprising
a) a nucleic acid sequence which is heterologous to said host
b) a prokaryotic signal sequence operably linked to said nucleic acid sequence, whereas said prokaryotic signal sequence is selected from signal peptides of periplasmatic binding proteins for sugars, amino acids, vitamins and ions and, whereas the expression of said nucleic acid sequence is controlled by said promoter region. The rhaBAD promoter is the preferred promoter region. More preferred, the isolated and purified nucleic acid sequence consists of SEQ ID NO. 1, a sequence complementary thereof and variants thereof, in particular the isolated and purified nucleic acid sequence consists of SEQ ID NO. 3, a sequence complementary thereof and variants thereof, most particular the isolated and purified nucleic acid sequence consists of SEQ ID NO. 4, a sequence complementary thereof and variants thereof.

The isolated and purified nucleic acid sequence of this invention can be isolated according to standard PCR protocols and methods well known in the art. Said purified and isolated DNA sequence can further comprise one or more regulatory sequences, as known in the art e.g. an enhancer, usually employed for the expression of the product encoded by the nucleic acid sequence.

In order to select host cells successfully and stably transformed with the vector or the isolated and purified nucleic acid sequence of the present invention, a gene that encodes a selectable marker (e.g., resistance to antibiotics) can be introduced into the host cells along with the nucleic acid sequence of interest. The gene that encodes a selectable marker might be located on the vector or on the isolated and purified nucleic acid sequence or might optionally be co-introduced in separate form e.g. on a separate vector. Various selectable markers can be used including those that confer resistance to antibiotics, such as hygromycin, ampicillin and tetracyclin. The amount of the antibiotic can be adapted as desired in order to create selective conditions. Usually, one selectable marker is used. As well reporter genes such as fluorescent proteins can be introduced into the host cells along with the nucleic acid sequence of interest, in order to determine the efficiency of transformation.

Another aspect of the present invention is to provide a prokaryotic host transformed with a vector of the present invention. In a particular embodiment of the invention the prokaryotic host is transformed with plasmid pBW22-Fab-H or plasmid pAKL14, preferably with plasmid pAKL14 comprising two different coding regions in its dicistronic expression cassette for expressing a secreted, heterodimeric protein in such host cell such as e.g. a Fab. Preferably such heterodimeric protein is a Fab. In another embodiment of the invention the prokaryotic host is transformed with the isolated and purified nucleic acid sequence of the present invention.

A wide variety of prokaryotic host cells can be used for the heterologous expression of the nucleic acid sequences of this invention. These hosts may include strains of Gram-negative cells such as E. coli and Pseudomonas, or Gram positive cells such as Bacillus and Streptomyces. Preferably, the host cell is a Gram-negative cell, more preferably an E. coli cell. E. coli which can be used are e.g. the strains TG1, W3110, DH1, XL1-Blue and Origami, which are commercially available or can be obtained via the DSMZ (Deutsche Sammlung von Mikroorganismen and Zellkulturen GmbH, Braunschweig, Germany). Most preferably, W3110 is used. The host cell might or might not metabolise L-rhamnose. A host cell which is ordinarily capable to uptake and metabolise L-rhamnose like E. coli might be modified to be deficient in one or more functions related to the uptake and/or metabolism of L-rhamnose. Deficiency in one or more functions related to the uptake and/or metabolism of L-rhamnose can be achieved by e.g. suppressing or blocking the expression of a gene coding for a protein related to the uptake and/or metabolism of L-rhamnose such as the gene rhaB coding for L-rhamnulose kinase. This can be done by known techniques such as transposon supported mutagenesis or knock-out mutation. Usually, the prokaryotic host corresponds to the signal sequences chosen, e.g. in case signal sequences of E. coli are used, the host cell is usually a member of the same family of the enterobacteriaceae, more preferably the host cell is an E. coli strain.

Further provided with the present invention is a method for producing a polypeptide in a host cell, comprising the steps of
a) constructing a vector,
b) transforming a prokaryotic host with said vector,
c) allowing expression of said polypeptide in a cell culture system under suitable conditions,
d) recovering said polypeptide from the cell culture system.

The vector used, as well as its construction and the transformation of a prokaryotic host are as defined above, whereas the heterologous nucleic acid sequence comprised by the vector encodes a polypeptide. Preferably, the polypeptide produced is an antibody and most preferably a Fab fragment, whereas the heavy and light chains of the antibody or the Fab fragment are expressed in the cell culture system in equal amounts, thus leading to high concentrations of functional antibody or Fab fragment.

As cell culture system continuous or discontinuous culture such as batch culture or fed batch culture can be applied in culture tubes, shake flasks or bacterial fermentors. Host cells are usually cultured in conventional media as known in the art such as complex media like "nutrient yeast broth medium" or a glycerol containing medium as described by Kortz et al., 1995, J. Biotechnol. 39, 59-65 or a mineral salt media as described by Kulla et al., 1983, Arch. Microbiol, 135, 1. The preferred medium for carrying out the expression of said polypeptide is a glycerol containing medium, more preferably the medium described by Kortz et al., 1995, J. Biotechnol. 39, 59-65.

The medium might be modified as appropriate e.g. by adding further ingredients such as buffers, salts, vitamins or amino acids. As well different media or combinations of media can be used during the culturing of the cells. Preferably, the medium used as basic medium should not include L-rhamnose, in order to achieve a tight regulation of the L-rhamnose promoter region. L-rhamnose is usually added after the culture has reached an appropriate $OD_{600}$ depending on the culture system. Usually, the amount of L-rhamnose in the medium of the cultured prokaryotic host is between 0.01 and 100 g/l, preferably between 0.1 and 10 g/l, more preferably 1 and 5 g/l. For batch culture the usual $OD_{600}$ is usually 0.4 or higher. Appropriate pH ranges are e.g. 6-8 preferably 7-7.5, appropriate culture temperatures are between 10 and 40, preferably between 20 and 37° C. The cells are incubated usually as long as it takes until the maximum amount of expressed product has accumulated, preferably between 1 hour and 20 days, more preferably between 5 hours and 3 days. The amount of expressed product depends on the culture system used. In shake flask culture usually expressed product in the amount of 0.5 g/l culture medium can be produced with a host transformed with the vector of the present invention. Using a fermentor culture in a batch and/or fed-batch mode expressed product in the amount of usually more than 0.5 g/l fermentation broth, preferably more than 1 g/l more preferably more than 1.3 g/l can be obtained.

Following expression in the host cell, the expressed product such as the polypeptide of interest can then be recovered from the culture of host cells. When the polypeptide of interest are immunoglobulin chains, the heavy chain and the light chain are normally each expressed in the host cell and secreted to the periplasm of the cell. The signal peptides encoded by the signal sequences in the expression vector are then processed from the immunoglobulin chains. The mature heavy and light chains are then assembled to form an intact antibody or a Fab fragment. In order to obtain a maximum yield of the expressed product the cells are usually harvested at the end of the culture and lysed, such as lysing by lysozyme treatment, sonication or French Press. Thus, the polypeptides are usually first obtained as crude lysate of the host cells. They can then be purified by standard protein purification procedures known in the art which may include differential precipitation, molecular sieve chromatography, ion-exchange chromatography, isoelectric focusing, gel electrophoresis, affinity, and immunoaffinity chromatography. These well known and routinely practiced methods are described in, e.g., Ausubel et al., supra., and Wu et al. (eds.), Academic Press Inc., N.Y.; Immunochemical Methods In Cell And Molecular Biology. For example, for purification of recombinantly produced immunoglobulins or Fab fragments, they can be purified with immunoaffinity chromatography by passage through a column containing a resin which has bound thereto target molecules to which the expressed immunoglobulins can specifically bind.

A further aspect of the present invention is a vector expressible in a host comprising a promoter region operably linked to a transcriptional unit comprising
a) a nucleic acid sequence which is heterologous to said host
b) a translation initiation region upstream of the initiation point of the translation of said transcriptional unit, said translation initiation region consisting of the sequence AGGAGATATACAT (SEQ ID NO. 2),
whereas said translation initiation region is operably linked to said nucleic acid sequence and the expression of said nucleic acid sequence is controlled by said promoter region. The promoter region might be an inducible or non-inducible promoter region. Usually, an inducible promoter region of a catabolic operon is used. As inducible promoter region of a catabolic operon negatively regulated promoter systems such as the lactose [lac] (Yanisch-Perron et al., 1985, Gene 33, 103-109), and the tryptophan [trp] (Goeddel et al., 1980, Nature (London) 287, 411-416) promoters, and the hybrid promoters derived from these two. [tac and trc] (Brosius, 1984, Gene 27:161-172; Amann and Brosius, 1985, Gene 40, 183-190) as well as positively regulated promoter systems such as the araB promoter inducible by Arabinose (WO 86 04356), the rhamnose promoter rhaSB inducible by rhamnose (WO 03068956) or the "rhaBAD promoter region of the L-rhamnose operon" of the present invention can be used. Preferably, positively regulated catabolic operons are used, more preferred is the "rhaBAD promoter region of the L-rhamnose operon" of the present invention. As well functional equivalents of these promoters which might be from various prokaryotic organisms might be used. Functional equivalents are in the case of positively regulated catabolic operons equivalents which in the presence of inducer show increased expression activity compared to their activity in the absence of inducer. The expression activity in the presence of inducer is usually at least two times, preferably at least five times, more preferably at least ten times higher than in the absence of the inducer.

Usually, the vector further comprises a signal sequence operably linked to said nucleic acid sequence. The signal sequence can be prokaryotic or eukaryotic. Preferably prokaryotic signal sequences are used. A prokaryotic signal sequence is preferably selected from signal peptides of periplasmatic binding proteins for sugars, amino acids, vitamins and ions as described above or from other prokaryotic signal sequence known to the person in the art. More preferably the prokaryotic signal sequence is selected from signal peptides of periplasmatic binding proteins for sugars, amino acids, vitamins and ions which are described above. Usually, the nucleic acid sequence encodes a polypeptide, preferably an antibody, more preferably a Fab fragment as described above.

In a particular embodiment, in case the nucleic acid sequence encodes an antibody, preferably a Fab fragment, the heavy and the light chain of the antibody, preferably of the Fab fragment are encoded by a dicistronic transcriptional unit, whereas each chain is operably linked to a signal sequence and the translation initiation region consisting of the sequence AGGAGATATACAT (SEQ ID NO. 2).

In a further aspect the present invention provides a method for producing a polypeptide in a host, comprising the steps of:
a) constructing a vector,
b) transforming a prokaryotic host with said vector,
c) allowing expression of said polypeptide in a cell culture system under suitable conditions,
d) recovering said polypeptide from the cell culture system.

Useful vectors and hosts are as described above. The construction of the vector, the transformation of a prokaryotic host and the cell culture can be conducted as described above, whereas the heterologous nucleic acid sequence comprised by the vector encodes a polypeptide. In case the polypeptide produced is a Fab fragment, the heavy and light chains of the Fab fragment are expressed in said cell culture system in equal amounts.

The present invention also relates to methods and means for the intracellular heterologous expression of nucleic acids encoding e.g. polypeptides in a prokaryotic host. In particular the present invention relates to vectors for the intracellular expression of a heterologous polypeptide in a prokaryotic host, whereby the vector is expressible in a prokaryotic host comprising the rhaBAD promoter region of the L-rhamnose operon operably linked to a transcriptional unit comprising a nucleic acid sequence which is heterologous to said host. Since in this embodiment of the vector of the present invention the nucleic acid sequence is not linked to a prokaryotic signal sequence upon transforming a prokaryotic host cell with the vector and expression of the polypeptide encoded by the heterologous nucleic acid the polypeptide will not be transported from the cytoplasm to non-cytoplasmic locations. Instead the polypeptide will be expressed within the cytoplasm in form of inclusion bodies or in soluble form. Thus upon expression the polypeptide can be isolated and purified by well-known procedures from the cell, in particular from cell extract. The present invention also provides for the use of said vectors for the regulated intracellular expression of a heterologous nucleic acid sequence in a prokaryotic host cell; a prokaryotic host or prokaryotic host cell transformed with said vector; a method for the intracellular production of a heterologous polypeptide in a prokaryotic host using said vector; and a vector for the intracellular production of a heterologous polypeptide comprising a promoter region, a heterologous nucleic acid sequence encoding a heterologous polypeptide and a translation initiation region consisting of the sequence AGGAGATATACAT (SEQ ID NO: 2).

In a preferred embodiment of the vector for the intracellular expression the rhaBAD promoter consists of the sequence depicted in SEQ ID No. 1, a sequence complementary thereof and a variant sequence thereof. It is preferred that said rhaBAD promoter region and said operably linked transcriptional unit consist of the sequence depicted in SEQ ID No. 3 or SEQ ID No. 4, a sequence complementary thereof or a variant sequence thereof. According to the invention it is possible that the vector for intracellular expression comprises a dicistronic transcriptional unit. In another preferred embodiment of the invention the transcriptional unit of the vector further comprises a translation initiation region upstream of the initiation point of the translation of said transcriptional unit, whereby the translation initiation region consists of the sequence AGGAGATATACAT (SEQ ID No. 2). In further preferred embodiments the vector for intracellular expression comprises a transcription termination region such as the rrnB transcriptional terminator sequence. According to the invention the heterologous nucleic acid sequence may encode a polypeptide such as an antibody, an antibody fragment etc.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein. Various references are cited throughout this Specification, each of which is incorporated herein by reference in its entirety.

The foregoing description will be more fully understood with reference to the following Examples. Such Examples, are, however, exemplary of methods of practising the present invention and are not intended to limit the scope of the invention.

EXAMPLES

Example 1

Construction of Expression Plasmids with Positively Regulated Promoters

The *Escherichia coli* W3110 genome was scanned for positively regulated operons. Based on the genomic data which are available on the KEGG database (Kyoto Encyclopedia of Genes and Genomes) positively regulated catabolic promoters were identified and analysed for their use in expression plasmids. The promoters should be tightly regulated and induced by a cheap and non-toxic and therefore industrially useful compound. The following promoters of different positively regulated catabolic operons were chosen prp promoter (propionate inducible)
gutA promoter (glucitol inducible)
melAB2 promoter (melibiose inducible)

The precise DNA fragments which contain the promoter elements were selected based on the available information on the corresponding regulator binding sites. Chromosomal DNA of *Escherichia coli* was isolated by the method of Pitcher et al., 1989, Letters in Applied Microbiology 8, 151-156. The promoter fragments were amplified from the chromosomal DNA of strain W3110 by PCR using the following primers. The restriction sites of ClaI and AflII are underlined. The sequences of the fragments are as follows:

```
Pprp      Pprp-5      5' aaa atc gat aaa tga aac gca tat ttg 3' (SEQ ID NO: 5)
          Pprp-3      5' aaa ctt aag ttg tta tca act tgt tat 3' (SEQ ID NO: 6)
AAAATCGATAACTGAAACGCATATTTGCGGATTAGTTCATGACTTTATCTCTAACAAA

TTGAAATTAAACATTTAATTTTATTAAGGCAATTGTGGCACACCCCTTGCTTTGTCTTT

ATCAACGCAAATAACAAGTTGATAACAACTTAAGTTT (SEQ ID NO: 7)

PgutA     PgutA-5     5' aaa atc gat gca tca cgc ccc gca caa 3' (SEQ ID NO: 8)
          PgutA-3     5' aaa ctt aag tca gga ttt att gtt tta 3' (SEQ ID NO: 9)
AAAATCGATGCATCACGCCCCGCACAAGGAAGCGGTAGTCACTGCCCGATACGGAC

TTTACATAACTCAACTCATTCCCCTCGCTATCCTTTTATTCAAACTTTCAAATTAAAATA

TTTATCTTTCATTTTGCGATCAAAATAACACTTTTAAATCTTTCAATCTGATTAGATTAG

GTTGCCGTTTGGTAATAAAACAATAAATCCTGACTTAAGTTT (SEQ ID NO: 10)

PmelAB2   PmelAB-5-1  5' aaa atc gat gac tgc gag tgg gag cac 3' (SEQ ID NO: 11)
          PmelAB-3    5' aaa ctt aag ggc ttg ctt gaa taa ctt 3' (SEQ ID NO: 12)
          MelR                              CRP
AAAATCGATACTCTGCTTTTCAGGTAATTTATTCCCATAAACTCAGATTTACTGCTGC

TT

CACGCAGGATCTGAGTTTATGGGAATGCTCAACCTGGAAGCCGGACGTTTTCTGCA

GATTCGCCTGCCATGATGAAGTTATTCAAGCAAGCCCTTAAGTTT (SEQ ID NO: 13)
                                +1
```

(Binding site for CRP 2 is highlighted in light grey and binding sites for MelR are highlighted in black)

The fragments were separated by agarose gelelectrophoresis and isolated by the gelextraction kit QiaexII from Qiagen (Hilden, Germany). The isolated fragments were cut with ClaI and AflII and ligated to ClaI/AflII-cut pBW22 (Wilms et al., 2001, Biotechnology and Bioengineering, 73 (2), 95-103). The resulting plasmids containing the prp promoter (pBLL5), the gutA promoter (pBLL6) and the melAB2 promoter (pBLL7) are identical except for the promoter region ligated. The sequence of the inserted promoter fragments were confirmed by sequencing (Microsynth GmbH, Balgach, Switzerland).

Example 2

Construction of Fab Fragment Expression Plasmids

Figure 2:
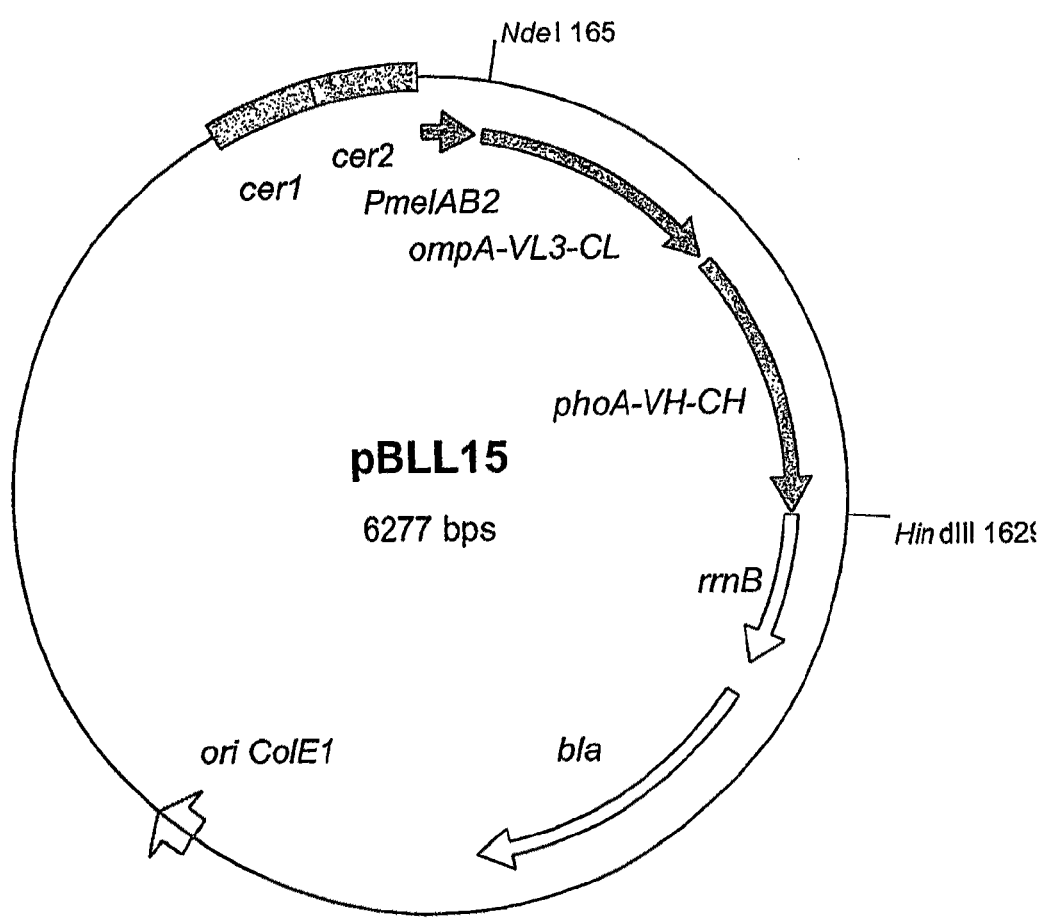
FIG. 2 shows plasmid pBLL15 containing a melibiose inducible promoter (PmelAB2), sequences coding for signal sequences operably linked to the light chain (ompA-VL3-CL) and the heavy chain (phoA-VH-CH) of a Fab fragment, and a transcription termination region (rrnB).

As an alternative to an IPTG-inducible lac promoter (plasmid pMx9-HuCAL-Fab-H, Knappik et al., 1985, Gene 33, 103-119), different positively regulated expression systems were analysed for their capacity to produce Fab-H antibody fragments. The Fab-H fragment was amplified out of plasmid pMx9-HuCAL-Fab-H by PCR using the primers Fab-5 (5'-aaa cat atg aaa aag aca gct atc-3' (SEQ ID NO: 14D and Fab-3 (5'-aaa aag ctt tta tca gct ttt cgg ttc-3' (SEQ ID NO: 15D. The PCR-fragment was cut with NdeI and HindIII and inserted into NdeI/HindIII-cut pBW22 (Volff et al., 1996, Mol. Microbiol. 21, 1037-1047) to create plasmid pBW22-Fab-H (FIG. 1) containing the rhamnose inducible rhaBAD promoter (SEQ ID NO. 1). The same PCR-fragment was inserted into the different expression plasmids with inducible promoters. The resulting Fab-H containing (putative) expression plasmids are pBLL13 containing the prp promoter, pBLL14 containing the gutA promoter and pBLL15 containing the melAB2 promoter (FIG. 2). The sequence of the Fab-H insert of plasmid pBW22-Fab-H was confirmed by sequencing.

Example 3

Expression of Fab Fragment

Strain W3110 (DSM 5911, Deutsche Sammlung von Mikroorganismen and Zellkulturen GmbH, Braunschweig, Germany) was transformed with the different expression plasmids. The plasmids were isolated from clones which resulted from the different transformations and checked via restriction analysis. Except plasmid pBLL14 all plasmids had the expected restriction pattern. The re-isolated plasmid pBLL14 showed an altered size and restriction pattern which was suggested to be due to recombination events. Therefore strain W3110 (pBLL14) was not tested in the following assays. The remaining strains were tested for their ability to secrete actively folded Fab-H antibody fragments. This productivity test was performed as described in example 4. The following inducers were added in a concentration of 0.2%

| pBW22-Fab-H | L(+)-Rhamnose monohydrate |
| pBLL13 | Sodium propionate |
| pBLL15 | D(+)-Melibiose monohydrate |
| | D(+)-Raffinose monohydrate |
| | D(+)-Galactose |

Figure 3:
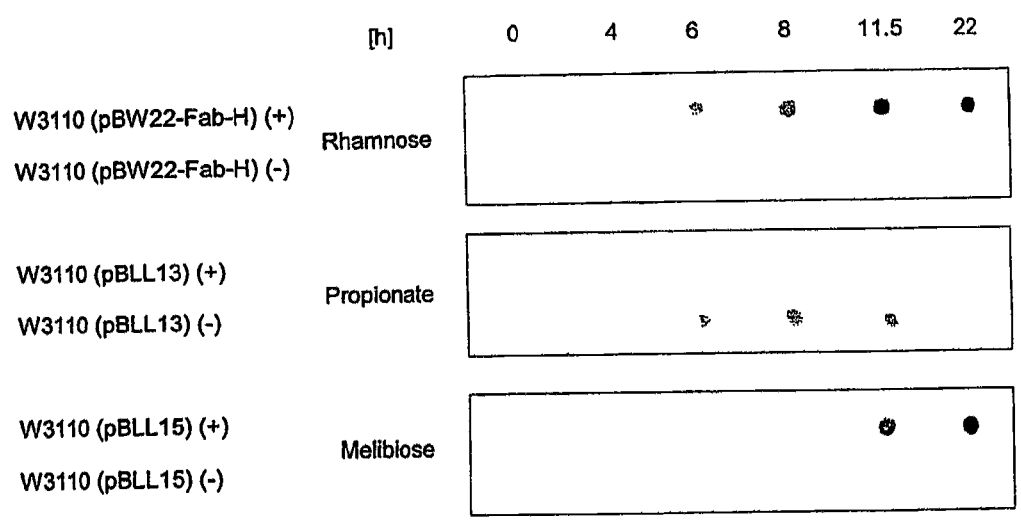
FIG. 3 shows dotblot results (with anti-human light chain for detecting Fab, alkaline peroxidase conjugated) of lysozyme extracts of the uninduced (−) and induced (+) W3110 strains with the different expression plasmids. The time intervals are indicated.

The results from the dot blot experiments are shown in FIG. 3.

The rhamnose- and melibiose-induced strains W3110 (pBW22-Fab-H) and W3110 (pBLL15) showed promising dot blot results: increasing signals over time and almost no background activity. The portion of actively folded antibody fragments was quantified via ELISA. The results are summarized in the following Table 1.

TABLE 1

ELISA results of the W3110 derivatives with the different expression plasmids. The time after induction is indicated. The uninduced cultures after 22 or 25 h were measured as uninduced controls and the results from strain W3110 (pMx9-HuCAL-Fab-H) and TG1F'-(pMx9-HuCAL-Fab-H) are used as references. The Fab-H concentration is given in mg/100 $OD_{600}$/L (n.d. not determined)

| Plasmid | Inducer | 8 h | 11.5/12 h induced | 22/25 h | 22/25 h uninduced |
|---|---|---|---|---|---|
| in TG1F'- | | | | | |
| pMx9-HuCAL-Fab-H | IPTG | nd | Nd | 68.64 | 84.56 |
| in W3110 | | | | | |
| pMx9-HuCAL-Fab-H | IPTG | nd | Nd | 140.56 | 8.14 |
| pBW22-Fab-H | Rhamnose | 176.88 | 259.56 | 328.62 | 6.52 |
| pBLL13 | Propionate | nd | 0.84 | 0.90 | 3.94 |
| pBLL15 | Melibiose | 2.89 | 145.10 | 504.28 | 4.28 |

All strains grew well without any growth inhibition in the presence or absence of the corresponding inducer up to $OD_{600}$ between 4 and 6. The expression plasmids pBW22-Fab-H (containing SEQ ID NO. 3) and pBLL15 led to the highest antibody fragment titers after overnight induction. The melibiose induced strain W3110 (pBLL15) showed a delayed increase in the formation of active antibody fragments compared to the rhamnose (pBW22-Fab-H) induced system.

The rhamnose inducible strain W3110 (pBW22-Fab-H) was tested in the Respiration Activity Monitoring System (RAMOS, ACBiotec, Jülich, Germany), a novel measuring system for the on-line determination of respiration activities in shake flasks. In comparison to the normal shake flask experiment the antibody titer (which was measured via ELISA) doubled (703.64 mg/L/100 $OD_{600}$ after 23 h of induction). The optimised growth using the RAMOS equipment favours the production of active antibody fragments.

Example 4

Melibiose Induction in Shake Flasks

E. coli W3110 carrying plasmid pBLL15 was tested for its capacity to produce actively folded Fab-H antibody fragments. Overnight cultures [in NYB medium (10 g/l tryptone, 5 g/l yeast extract, 5 g/l sodium chloride) supplemented with 100 μg/ml of Ampicillin, 37° C.] were diluted (1:50) in 20 ml of fresh glycerol medium (as described by Kortz et al., 1995, J. Biotechnol. 39, 59-65, whereas the vitamin solution was used as described by Kulla et al., 1983, Arch. Microbiol, 135, 1 and incubated at 30° C. Melibose (0.2%) was added when the cultures reached an $OD_{600}$ of about 0.4. Samples (1 ml) were taken at different time intervals, centrifuged and the pellets were stored at −20° C. The frozen cells were lysed according to the above described lysozyme treatment and the supernatants were analysed in dot blot and ELISA assays. 504,28 mg/L/100 $OD_{600}$ of functional Fab-H antibody fragments were obtained.

Example 5

Occurrence of High Molecular Weight Aggregates

In order to find out if high molecular weight aggregates are produced, western blot of extracts of strain W3110 (pBLL15), which showed the highest antibody titer (Table 1), was conducted using the anti-human Fab-H+AP conjugate. The culture was performed as described in example 4.

Samples were taken after 9, 12 and 23 hours after induction with melibiose. Lower concentrations of high molecular weight aggregates correspond to higher titers of functional antibody fragments. The choice of the expression system seems to influence the way in which the antibody fragments are formed: functional or in aggregates.

Example 6

Influence of Signal Peptides

The genome database of E. coli was used to look for useful signal peptides that could be used in combination with the Fab-H fragments VL3-CL and VH-CH. The signal sequences from periplasmic binding proteins for sugars, amino acids, vitamins and ions were chosen. These periplasmic proteins represent a relatively homogeneous group that have been more extensively studied than other periplasmic proteins. Since they are generally abundant their signal sequences have to ensure an efficient transport over the inner membrane into the periplasm. All possible signal peptide Fab combinations were checked for their sequence peptide and cleavage site probability using the SignalP web server (http://www.cbs.d-tu.dk/services/SignalP-2.0/#submission) as shown in the following Table 2.

| Signal peptide (SEQ ID NOS 16-64, respectively, in order of appearance) | Signal peptide probability | Max Cleavage Site Probability |
|---|---|---|
| OmpA (*E. coli*)-Outer membrane protein a precursor | | |
| MKKTA IAIAV ALAGF ATVAQ A    APKDN (OmpA) | 1.000 | 0.993 |
| MKKTA IAIAV ALAGF ATVAQ A    DIELT (OmpA-VL3-CL, Fab-H) | 1.000 | 0.971 |
| | | |
| PhoA (*E. coli*)-Alkaline phosphatase precursor | | |
| VKQST IALAL LPLLF TPVTK A    RTPEM (PhoA) | 0.996 | 0.765 |
| MKQST IALAL LPLLF TPVTK A    QVQLK (PhoA-VH-CH, Fab-H) | 0.999 | 0.784 |
| | | |
| PelB (*Erwinia chrysantemi*)-Pectate lyase precursor | | |
| MKSLI TPITA GLLLA LSQPL LA    ATDTG (PelB) | 1.000 | 0.999 |
| MKSLI TPITA GLLLA LSQPL LA    DIELT (PelB-VL3-CL, Fab-H) | 1.000 | 0.998 |
| MKSLI TPITA GLLLA LSQPL LA    QVQLK (PelB-VH-CH, Fab-H) | 1.000 | 0.998 |
| | | |
| PelB (*Erwinia carotovora*)-Pectate lyase precursor | | |
| MKYLL PTAAA GLLLL AAQPA MA    ANTGG (PelB) | 1.000 | 1.000 |
| MKYLL PTAAA GLLLL AAQPA MA    DIELT (PelB-VL3-CL, Fab-H) | 1.000 | 1.000 |
| MKYLL PTAAA GLLLL AAQPA MA    QVQLK (PelB-VH-CH, Fab-H) | 1.000 | 1.000 |
| | | |
| PelB (*Xanthomonas campestris*)-Pectate lyase precursor | | |
| MRPKF STAAA ASLFV GSLLV IGVAS A    DPALE (PelB) | 1.000 | 0.993 |
| MKPKF STAAA ASLFV GSLLV IGVAS A    DIELT (PelB-VL3-CL, Fab-H) | 1.000 | 0.985 |
| MKPKF STAAA ASLFV GSLLV IGVAS A    QVQLK (PelB-VH-CH, Fab-H) | 1.000 | 0.988 |
| | | |
| LamB (*E. coli*)-Maltoporin precursor (Lambda receptor protein) | | |
| MMITL RKLPL AVAVA AGVMS AQAMA    VDFHG (LamB) | 1.000 | 0.975 |
| MMITL RKLPL AVAVA AGVMS AQAMA    DIELT (LamB-VL3-CL, Fab-H) | 1.000 | 0.979 |
| MMITL RKLPL AVAVA AGVMS AQAMA    QVQLK (LamB-VH-CH, Fab-H) | 1.000 | 0.988 |
| | | |
| MalE (*E. coli*)-Maltose-binding protein precursor | | |
| MKIKT GARIL ALSAL TTMMF SASAL A    KIEEG (MalE) | 1.000 | 0.956 |
| MKIKT GARIL ALSAL TTMMF SASAL A    DIELT (MalE-VL3-CL, Fab-H) | 1.000 | 0.978 |
| MKIKT GARIL ALSAL TTMMF SASAL A    QVQLK (MalE-VH-CH, Fab-H) | 1.000 | 0.990 |
| | | |
| Bla (pBR322) (*E. coli*)-Beta-lactamase | | |
| MSIQH FRVAL IPFFA AFCLP VFA    HPETL (Bla) | 1.000 | 1.000 |
| MSIQH FRVAL IPFFA AFCLP VFA    DIELT (Bla-VL3-CL, Fab-H) | 1.000 | 1.000 |
| MSIQH FRVAL IPFFA AFCLP VFA    QVQLK (Bla-VH-CH, Fab-H) | 1.000 | 0.999 |
| | | |
| OppA (*E. coli*)-Periplasmic oligopeptide-binding protein | | |
| MTNIT KRSLV AAGVL AALMA GNVAL A    ADVPA (OppA) | 1.000 | 0.996 |
| MTNIT KRSLV AAGVL AALMA GNVAL A    DIELT (OppA-VL3-CL, Fab-H) | 1.000 | 0.911 |
| MTNIT KRSLV AAGVL AALMA GNVAL A    QVQLK (OppA-VH-CH, Fab-H) | 1.000 | 0.984 |
| | | |
| TreA (*E. coli*)-Periplasmic trehalase precursor (Alpha-trehalose glucohydrolase | | |
| MKSPA PSRPQ KMALI PACIF LCFAA    EETPV (TreA) LSVQA | 1.000 | 0.996 |
| MKSPA PSRPQ KMALI PACIF LCFAA    DIELT (TreA-VL3-CL, Fab-H) LSVQA | 1.000 | 0.961 |
| MKSPA PSRPQ EMALI PACIF LCFAA    QVQLK (TreA-VH-CH, Fab-H) LSVQA | 1.000 | 0.989 |
| | | |
| MppA (*E. coli*)-Periplasmic murein peptide-binding protein precursor | | |
| MKHSV SVTCC ALLVS SISLS YA    AEVPS (MppA) | 1.000 | 0.943 |
| MKHSV SVTCC ALLVS SISLS YA    DIELT (MppA-VL3-CL, Fab-H) | 1.000 | 0.906 |
| MKHSV SVTCC ALLVS SISLS YA    QVQLK (MppA-VH-CH, Fab-H) | 1.000 | 0.938 |
| | | |
| BglX (*E. coli*)-Periplasmic beta-glucosidase precursor | | |
| MKWLC SVGIA VSLAL QPALA    DDLFG (BglX) | 1.000 | 0.999 |

```
                                                                      Max
                                                          Signal    Cleavage
                                                          peptide     Site
Signal peptide                                             prob-     Prob-
(SEQ ID NOS 16-64, respectively, in order of appearance)  ability   ability MKWLC SVGIA VSLAL QPALA          DIELT (BglX-VL3-CL, Fab-H)  0.999    0.999
MKWLC SVGIA VSLAL QPALA          QVQLK (BglX-VH-CH, Fab-H)   1.000    0.996

ArgT (E. coli)-Lysine-arginine-ornithine-binding periplasmic protein precursor
MKKSI LALSL LVGLS TAASS YA       ALPET                       1.000    0.929
MKKSI LALSL LVGLS TAASS YA       DIELT (ArgT-VL3-CL, Fab-H)  1.000    0.947
MKKSI LALSL LVGLS TAASS YA       QVQLK (ArgT-VH-CH, Fab-H)   1.000    0.960

MalS (E. coli)-Alpha-amylase precursor
MKLAA CFLTL LPGFA VA             ASWTS (MalS)                1.000    0.794
MKLAA CFLTL LPGFA VA             DIELT (MalS-VL3-CL, Fab-H)  0.998    0.995
MKLAA CFLTL LPGFA VA             QVQLK (MalS-VH-CH, Fab-H)   1.000    0.990

HisJ (E. coli)-Histidine-binding periplasmic protein precursor
MKKLV LSLSL VLAFS SATAA FA       AIPQN (HisJ)                1.000    0.994
MKKEV LSLSL VLAFS SATAA FA       DIELT (HisJ-VL3-CL, Fab-H)  1.000    0.957
MKKLV LSLSL VLAFS SATAA FA       QVQLK (HisJ-VH-CH, Fab-H)   1.000    0.988

XylF (E. coli)-D-Xylose-binding periplasmic protein precursor
MKIKN ILLTL CTSLL LTNVA AHA      KEVKI (XylF)                1.000    0.996
MKIKN ILLTL CTSLL LTNVA AHA      DIELT (XylF-VL3-CL, Fab-H)  1.000    0.992
MKIKN ILLTL CTSLL LTNVA AHA      QVQLK (XylF-VH-CH, Fab-H)   1.000    0.996

FecB (E. coli)-Iron(III) dicitrate-binding periplasmic protein precursor
MLAFI RFLFA GLLLV ISHAF A        ATVQD (FecB)                1.000    0.975
MLAFI RFLFA GLLLV ISHAF A        DIELT (FecB-VL3-CL, Fab-H)  1.000    0.989
MLAFI RFLFA GLLLV ISHAF A        QVQLK (FecB-VH-CH, Fab-H)   1.000    0.990
```

The following six combinations were chosen:

LamB-VL3-CL (Maltoporin precursor)
MalE-VH-CH (Maltose-binding protein precursor)
Bla-VL3-CL (Beta-lactamase)
TreA-VH-CH (Periplasmic trehalase precursor)
ArgT-VL3-CL (Lysine-arginine-ornithine-binding periplasmic protein precursor)
FecB-VH-CH (Iron (III) dicitrate-binding periplasmic protein precursor)

The gene fusions to generate signal peptide (SP) to VL3-CL and VH-CH fusions were carried out with overlapping PCR primers and are summarized in the following amplification Table 3

| Primer | Template | Fragment |
|---|---|---|
| LamB-VL3-CL | | |
| lamB-5 | Genomic DNA of E. coli | lamB-SP |
| lamB-3 | W3110 | |
| lamB-VL3-5 VL3-3 | pMx9-HuCAL-Fab-H-S-S | VL3-CL |
| lamB-5 VL3-3 | lamB-SP/VL3-CL | lamB-VL3-CL |
| MalE-VH-CH | | |
| malE-5 | Genomic DNA of E. coli | malE-SP |
| malE-3 | W3110 | |
| malE-VH-CH VH-3 | pMx9-HuCAL-Fab-H | VH-CH |
| malE-5 VL3-3 | malE-SP/VH-CH | malE-VH-CH |
| Bla-VL3-CL | | |
| bla-5 | Genomic DNA of E. coli | bla-SP |
| bla-3 | W3110 | |
| bla-VL3-5 VL3-3 | pMx9-HuCAL-Fab-H-S-S | VL3-CL |
| bla-5 VL3-3 | bla-SP/VL3-CL | bla-VL3-CL |
| TreA-VH-CH | | |
| treA-5 | Genomic DNA of E. coli | treA-SP |
| treA-3 | W3110 | |
| treA-VH-CH VH-3 | pMx9-HuCAL-Fab-H-S-S | VH-CH |
| treA-5 VH-3 | treA-SP/VH-CH | treA-VH-CH |
| ArgT-VL3-CL | | |
| argT-5 | Genomic DNA of E. coli | argT-SP |
| argT-3 | W3110 | |
| argT-VL3-5 VL3-3 | pMx9-HuCAL-Fab-H | VL3-CL |
| argT-5 VL3-3 | argT-SP/VL3-CL | argT-VL3-CL |
| FecB-VH-CH | | |
| fecB-5 | Genomic DNA of E. coli | fecB-SP |
| fecB-3 | W3110 | |
| fecB-VH-CH VL3-3 | pMx9-HuCAL-Fab-H-S-S | VH-CH |
| fecB-5 VL3-3 | fecB-SP/VH-CH | fecB-VH-CH |

Figure 4:
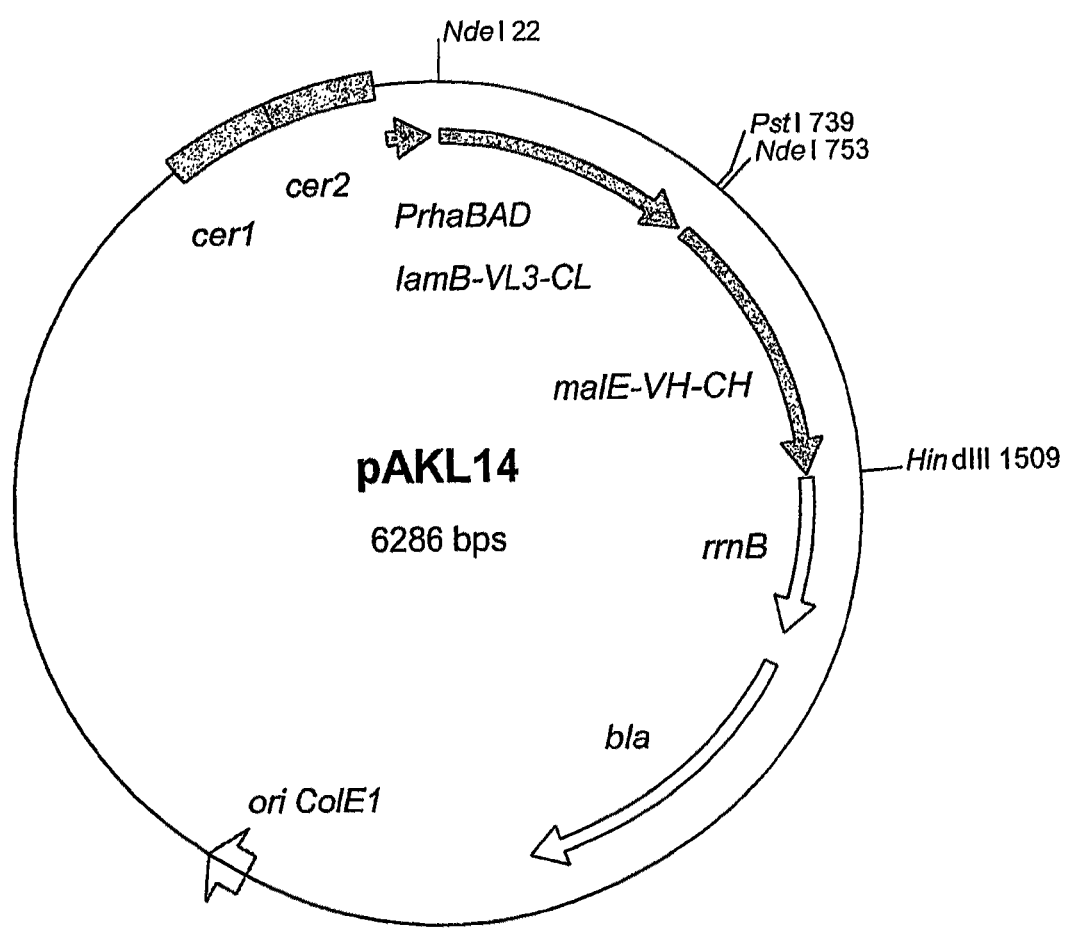
FIG. 4 shows plasmid pAKL14 containing the L-rhamnose inducible promoter (PrhaBAD) and the Fab-H genes with altered signal sequences.
Figure 8:
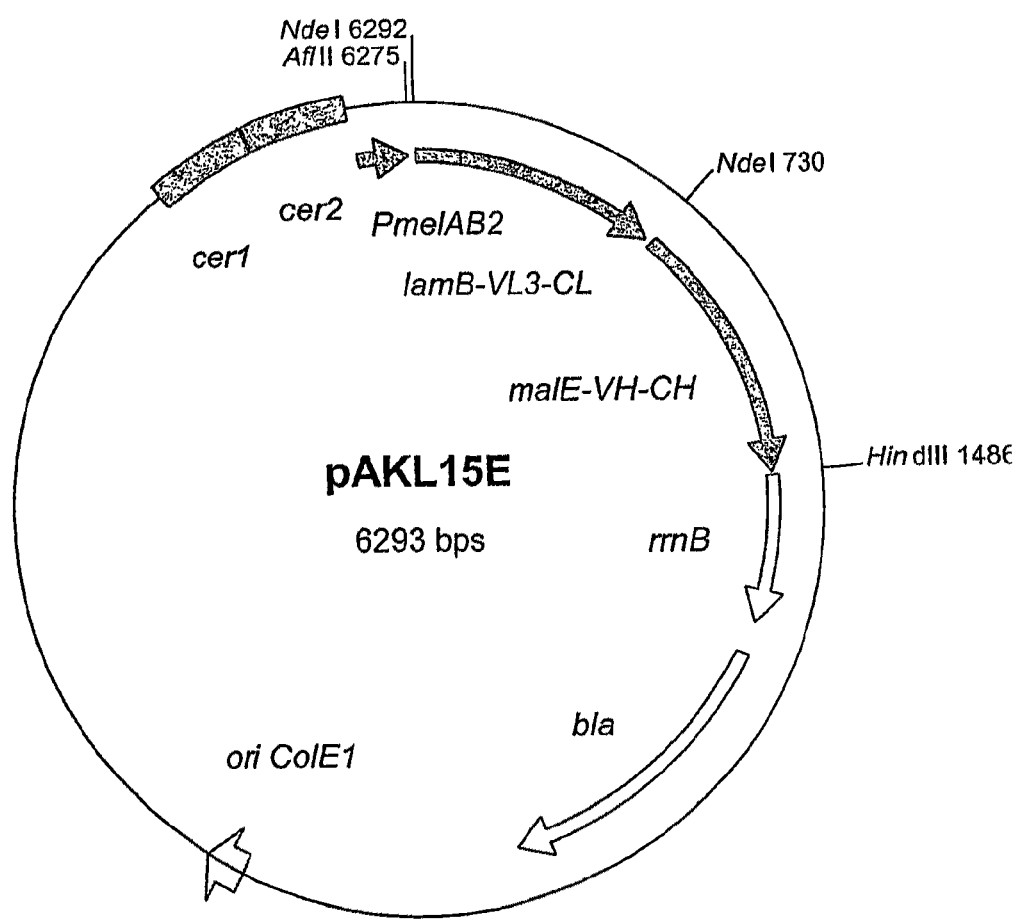
FIG. 8 shows plasmid pAKL15E containing the melibiose inducible promoter (PmelAB2) and the Fab-H genes with altered signal sequences.

The fusions of the signal peptide sequences with the VL3-CL and VH-CH sequences were performed as described elsewhere (Horton, R. M., Hunt, H. D., Ho, S. N., Pullen, J. K. and Pease, L. R. (1989) Engineering hybrid genes without the use of restriction enzymes: gene splicing by overlap extension. Gene 77, 61-68). The SP-VL3-CL genes were cut with restriction enzymes NdeI and PstI and ligated into NdeI/PstI cut pBW22 and into pBLL7. The resulting plasmids were cut with PstI and HindIII and ligated to PstI/HindIII cut SP-VH-CH genes. Since the integration of the bla-VL3-CL and fecB- VH-CH genes was not possible only the Fab-H expression plasmid containing the lamB-VL3-CL and malE-VH-CH genes could be tested. A lamB-VL3-CL/malE-VH-CH expression plasmid containing the rhamnose inducible promoter (pAKL14) was obtained. The lamB-VL3-CL/malE-VH-CH genes which were isolated from plasmid pAKL15 (example 7) as AflII/HindIII fragment were ligated into AflII/HindIII-cut pBLL7 to obtain pAKL15E. FIGS. 4 and 8 illustrate the lamB-VL3-CL/malE-VH-CH expression plasmids pAKL14 and pAKL15E.

Example 7

Influence of Translation Initiation Regions on Fab Expression

The Fab-H genes of plasmid pAKL14 (containing SEQ ID NO. 4) and plasmid pAKL15E contain the same DNA sequence 5' of the start codon (translation initiation region) whereas in the original plasmid pMx9-HuCAL-Fab-H the translation initiation regions of both Fab-H genes are different. A comparison of the translation initiation regions sequences of plasmid pMx9-HuCAL-Fab-H and pAKL14/pAKL15E is shown in the following Table 4:

| | | | | |
|---|---|---|---|---|
| pMx9-HuCAL-Fab-H | ompA-VL3-CL | gagggcaaaaa | atg | (SEQ ID NO: 65) |
| | phoA-VH-CH | aggagaaaataaa | atg | (SEQ ID NO: 66) |
| pAKL14/pAKL15E | lamB-VL3-CL | aggagatatacat | atg | (SEQ ID NO: 67) |
| | malE-VH-CH | aggagatatacat | atg | (SEQ ID NO: 67) |

Figure 5:
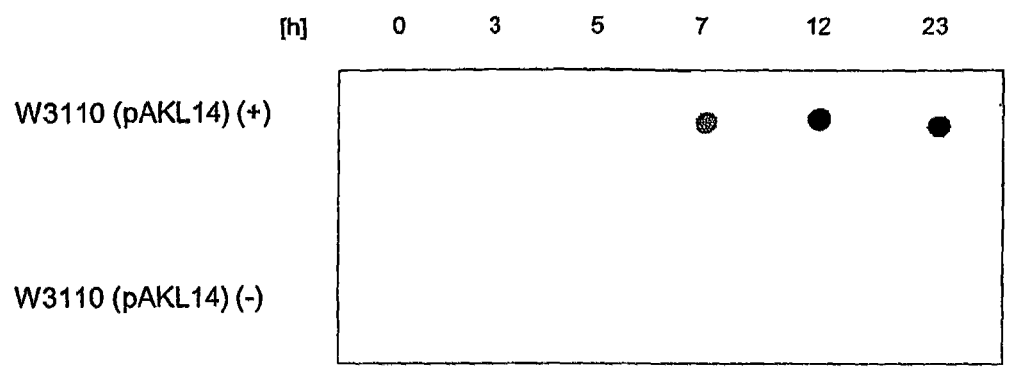
FIG. 5 shows dot blot of lysozyme extracts of uninduced (−) and L-rhamnose induced strain W3110 (pAKL14). The time when samples were taken is indicated (with anti-human light chain for detecting Fab, alkaline peroxidase conjugated).

The productivity of strain W3110 (pAKL14) was tested in shake flasks as described in example 4. The strain grew well in the presence or absence of L-rhamnose. That means the production of Fab-H did not influence the viability of the cells. As shown in FIG. 5 the dot blot results looked promising.

Figure 6:
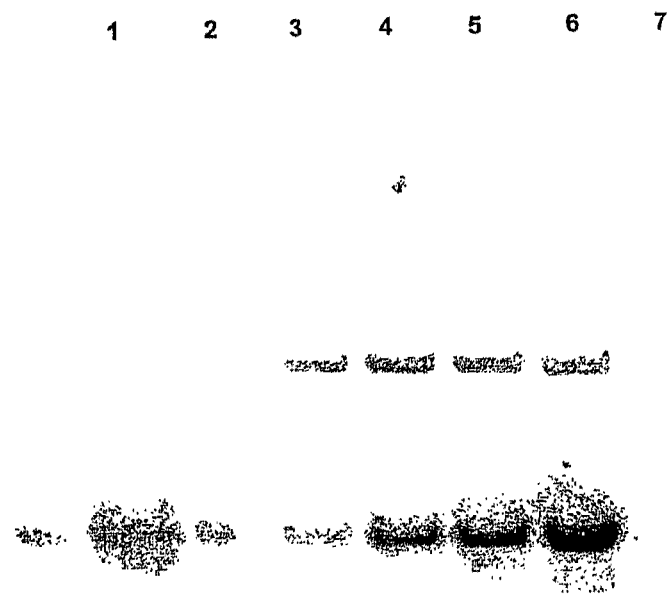
FIG. 6 shows a Western blot of lysozyme extracts of L-rhamnose induced strain W3110 (pAKL14). The time after induction when the samples were taken is indicated (with anti-human light chain for detecting Fab, alkaline peroxidase conjugated). Lane 1: Standard (1.28 µg); lane 2: W3110 (pAKL14), ind., 3 h; lane 3: W3110 (pAKL14), ind., 5 h; lane 4: W3110 (pAKL14), ind., 7 h; lane 5: W3110 (pAKL14), ind., 12 h; lane 6: W3110 (pAKL14), ind., 23 h; lane 7: W3110 (pAKL14), not ind., 23 h.

To analyse the presence of non-reducible high molecular weight aggregates a Western blot was performed (FIG. 6). Although high molecular weight aggregates appear after an induction time of 5 hours their amount only slightly increases after 23 h. The non-induced culture shows high molecular weight bands which might be due to a weak unspecific background production. The corresponding ELISA values are given in the following Table 5 (Fab-H concentration (mg/L/100 OD$_{600}$) in lysozyme extracts of uninduced and rhamnose induced strain W3110 (pAKL14)).

| Plasmid | Inducer | 5 h | 7 h induced | 12 h | 23 h | 23 h uninduced |
|---|---|---|---|---|---|---|
| in W3110 | Rhamnose | 29.04 | 267.48 | 308.40 | 596.14 | 2.84 |

The new signal peptide constructs (in combination with the modified translation initiation signals) again increased the antibody fragment titer from 328.62 mg/U100 OD$_{600}$ (plasmid pBW22-Fab-H which contains the MOR gene construct from plasmid pMx9-HuCAL-Fab-H) to 596.14 mg/U100 OD$_{600}$ (plasmid pAKL14) and to 878.86 mg/U100 OD$_{600}$ (plasmid pAKL15E). The sequencing of the lamb-VL3-CL and malE-VH-CH genes in pAKL14 revealed three base exchanges which are supposed to be due to the construction of the fusion genes by two consecutive PCR reactions. The base exchanges led to the following amino acid changes (the wrong amino acids are emphasized):

VL3-CL (pAKL14)-pI = 4.85
(SEQ ID NO: 68)
MMITLRKLPLAVAVAAGVMSAQAMADIELTQPPSVSVAPGQTARISCSGN
ALGDKYASWYQQNPGQAPVLVTYDDSDRPSGIPERFSGSNSGNTATLTIS
GTQAEDEADYYCQSYDSPQVVFGGGTKLTVLGQPKAAPSVTLFPPSSEEL
QANKATLVCLISDFYPGAVTVAWKADSSPVKAGVETTTPSKQSNNKYAAS
SYLSLTPEQWKSHRSYSCQVTHEGSTVEKTVAPTEA

VH-CH (pAKL14)-pI = 9.52
(SEQ ID NO: 69)
MKIKTGARILALSALTTMMFSASALAQVQLKESGPALVKPTQTLTLTCTF
SGFSLSTSGVGVGWIRQPPGKALEWLALIDWDDDKYYSTSLKTRLTISKD
TSKNQVVLTMTNMDPVDTATYYCARYPVTQRSYMDVWGQGTLVTVSSAST
KGPSVLPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKS

The light chain of Fab-H carries two mistakes (D50N, K63N) and the heavy chain one amino acid exchange (F156L). To restore the original Fab-H sequence two fragments from plasmid pAKL14 (138 by SexAI/BamHI and 310 by BssHII/HindIII fragment) were exchanged against the homologous fragments of plasmid pBW22-Fab-H (which carries the unchanged Fab-H gene sequence). The resulting plasmid pAKL15 carries the correct Fab-H sequence. The exchange of the three amino acids had no apparent effect on the overall Fab-H properties since the pI was unchanged. Therefore the capacity of strain W3110 (pAKL15) to produce functional Fab-H antibody fragments was supposed to be similar to strain W3110 (pAKL14) and was not analysed.

The Fab-H antibody fragment productivity could be increased by using different optimisation strategies. The following Table 6 summarizes the improvements:

| Strain | Improvement | Concentration of functional Fab-H Antibody (mg/L/100 OD$_{600}$) | Activity increase |
|---|---|---|---|
| TG1F'-(pMx9-HuCAL-Fab-H) | MOR strain | 84.56 | |
| W3110 (pMx9-HuCAL-Fab-H) | Strain background | 140.45 | 1.7 |
| W3110 (pBW22-Fab-H) | Expression system (Rhamnose) | 328.62 | 3.9 |
| W3110 (pBLL15) | Expression system (Melibiose) | 504.28 | 6 |
| W3110 (pAKL14) | Signal peptide Translation (Rhamnose) | 596.14 | 7 |
| W3110 (pAKL15E) | Signal peptide Translation (Melibiose) | 878.86 | 10.4 |

Figure 7:
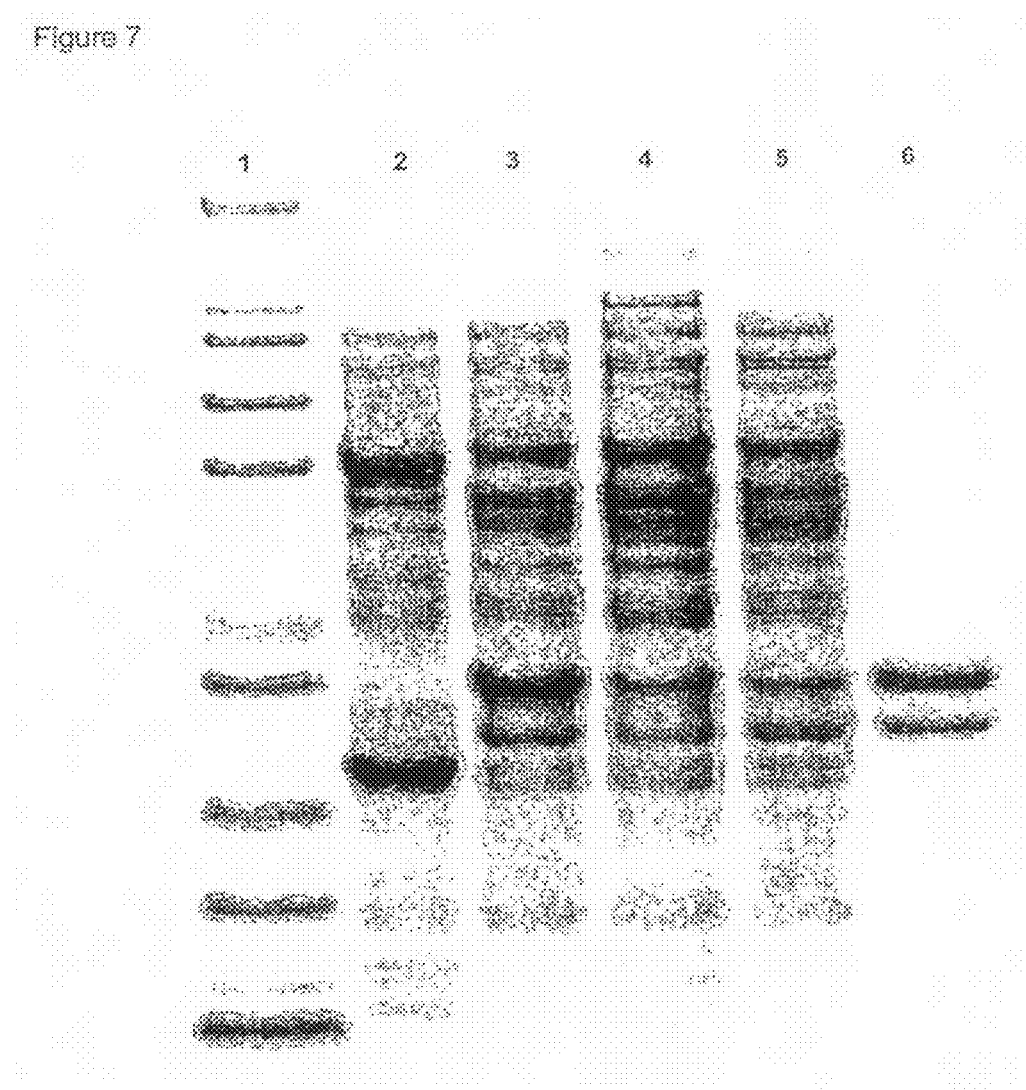
FIG. 7 shows SDS-PAGE of lysozyme extracts of different W3110 strains with high Fab-H antibody concentrations. The strains producing the light and heavy chain without signal sequences are used as a negative reference (lane 1: Marker; lane 2: W3110 (pMx9-HuCAL-Fab-H); lane 3: W3110 (pBW22-Fab-H); lane 4: W3110 (pBLL15), lane 5: W3110 (pAKL14); lane 6: Standard (2 µg)).

Strains which produced high Fab-H antibody titers were analysed via SDS-PAGE (FIG. 7). The highest functional Fab-H concentrations were measured in strains which produce a balanced amount of light and heavy chain (lanes 4 and 5). The rhamnose inducible strains which carry the Fab-H fragment such as W3110 (pBW22-Fab-H) (lane 3) strongly overproduce the light chain.

Example 8

Melibiose Induction in Shake Flasks

Figure 9:
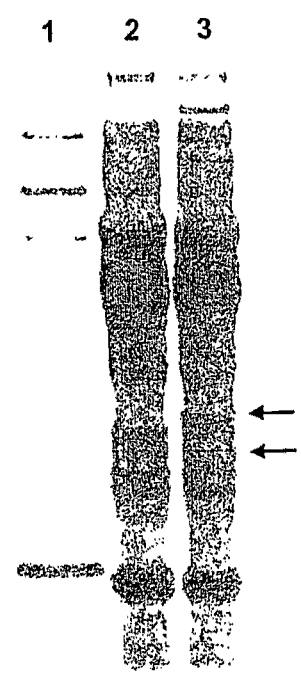
FIG. 9: shows SDS-PAGE of lysozyme extracts of strain W3110 (pAKL15E) in the presence or absence of the inducer melibiose. The position of the light and heavy chain is indicated (lane 1: Marker; lane 2: W3110 (pAKL15E), not induced; lane 3: W3110 (pAKL15E), induced).

E. coli W3110 carrying plasmid pAKL15E (FIG. 8) was tested for its capacity to produce actively folded Fab-H antibody fragments. Overnight cultures [in NYB medium (10 g/l tryptone, 5 g/l yeast extract, 5 g/l sodium chloride) supplemented with 100 µg/ml of Ampicillin, 37° C.] were diluted (1:50) in 20 ml of fresh glycerol medium (as described by Kortz et al., 1995, J. Biotechnol. 39, 59-65, whereas the vitamin solution was used as described by Kulla et al., 1983, Arch. Microbiol, 135, 1 and incubated at 30° C. Melibose (0.2%) was added when the cultures reached an $OD_{600}$ of about 0.4. Samples (1 ml) were taken at different time intervals, centrifuged and the pellets were stored at −20° C. The frozen cells were lysed according to the above described lysozyme treatment and the supernatants were analysed in SDS-PAGE and ELISA assays. The melibiose inducible strain which carry the Fab-H genes with the altered signal peptides (lamB-VL3-CL/malE-VH-CH) showed the highest Fab-H antibody titers (Table 6). The light and heavy chain of Fab-H were produced in equal amounts (FIG. 9).

Example 9

Intracellular Production of Antibody Fragments

Origami host strains provide mutations in both the thioredoxin reductase (trxB) and glutathione reductase (gor) genes, enhancing disulfide bond formation and permit protein folding in the bacterial cytoplasm. To construct the VL3-CL and VH-CH genes without signal peptide regions the following primers were used:

```
5'-VL5'-aaa cat atg gat atc gaa ctg acc cag-3' (SEQ ID NO:    (NdeI restriction site)
    70)

3'-CL5'-aaa ctg cag tta tca ggc ctc agt cgg-3'(SEQ ID NO: 71) (PstI restriction site)

5'-VH5'-aaa ctg cag gag ata tac ata tgc agg tgc aat tga a-3') (PstI restriction site)
    (SEQ ID NO: 72)

3'-CH5'-aaa aag ctt tta tca gct ttt cgg ttc-3'(SEQ ID NO: 73) (HindIII restriction site)
```

The corresponding VL3-CL and VH-CH genes were amplified and checked via restriction analysis. The NdeI/PstI cut VL3-CH fragment was integrated into NdeI/PstI cut plasmid pBW22. The resulting plasmid was cut with PstI and HindIII and ligated to the PstI/HindIII cut VH-CH fragment to get plasmid pJKL6. The plasmid was transformed into the Origami strain and strain W3110 as a reference. The productivity of the strains W3110 (pJKL6) and Origami (pJKL6) was tested in shake flasks as described in example 4.

To analyse the presence of functional antibody fragments and non-reducible high molecular weight aggregates a Western blot was performed. Both strains hardly produce any functional antibody fragments. Strain W3110 accumulates high molecular weight aggregates with increasing induction times (W3110) whereas the Origami strain does not produce any antibody fragments. The corresponding ELISA values are given in the following Table 7 (Fab-H concentration (mg/L/100 $OD_{600}$) in lysozyme extracts of uninduced and rhamnose induced strains Origami (pJKL6) and W3110 (pJKL6)):

| Plasmid | Inducer | 7 h induced | 11 h induced | 24 h induced | 24 h uninduced |
|---|---|---|---|---|---|
| Origami | | | | | |
| pJKL6 W3110 | Rhamnose | 5.24 | 6.86 | 10.54 | 2.60 |
| pJKL6 | Rhamnose | 2.73 | 5.34 | 5.2 | 2.83 |

Example 10

Rhamnose Induction of a Single Chain Antibody (scFv, S1) in Shake Flasks

Figure 10:
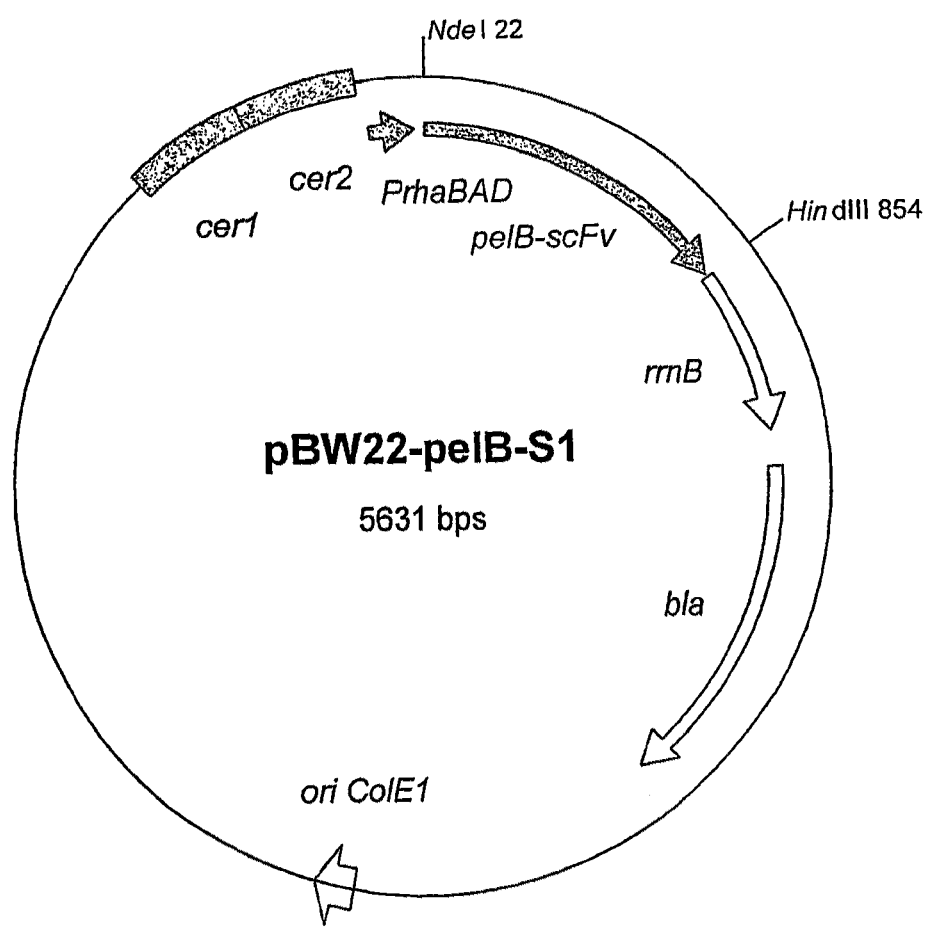
FIG. 10 shows plasmid pBW22-pelB-S1 comprising the L-rhamnose inducible rhaBAD promoter, a sequence coding for a PelB signal peptide operably linked to a sequence coding for a single chain antibody (scFv, S1), and a transcription termination region (rrnB).
Figure 11:
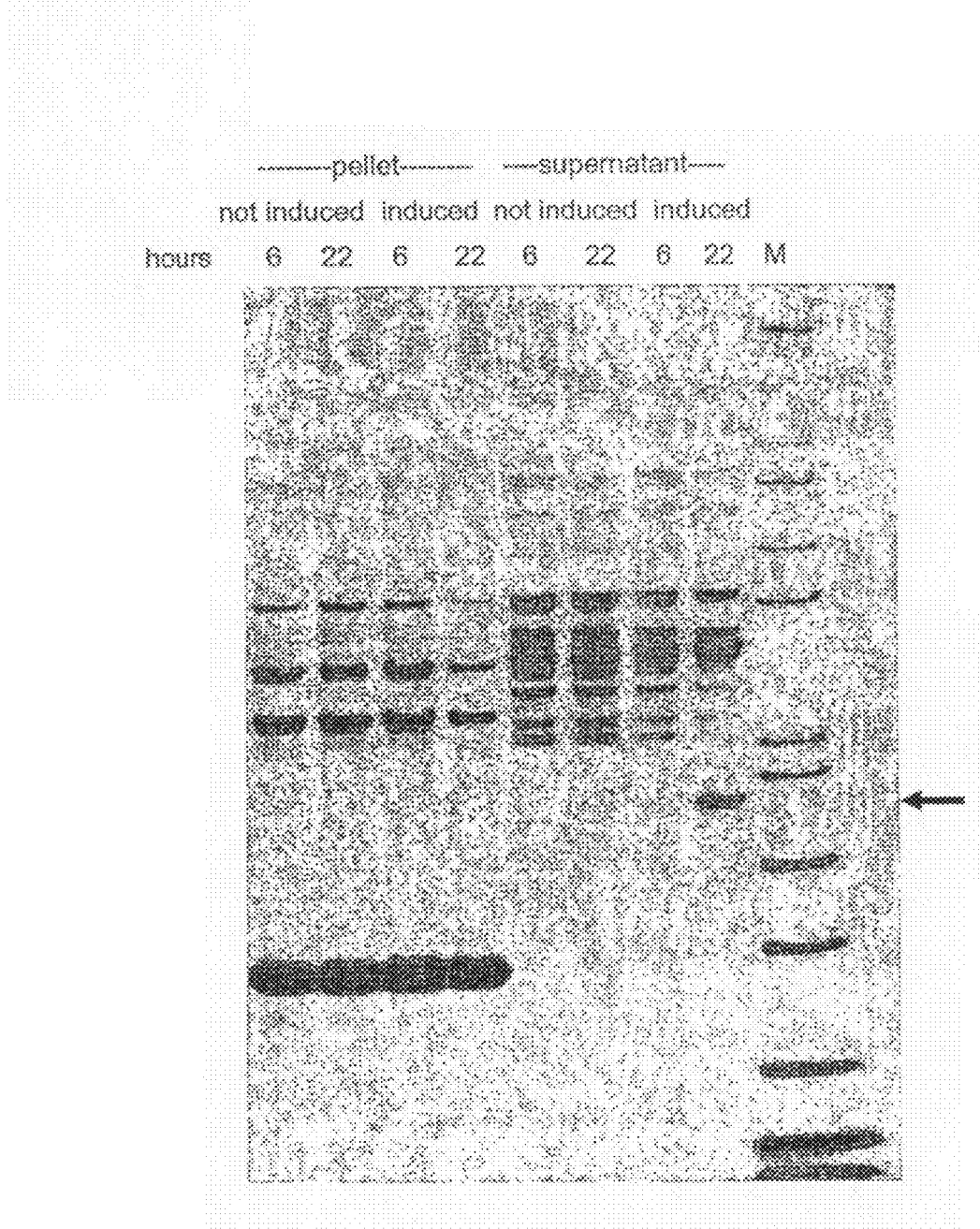
FIG. 11 shows SDS-PAGE for crude extracts of not induced (−) and induced (+) strain W3110 (pBW22-pelB-S1). Samples were taken after different time intervals as indicated. The soluble and insoluble protein fractions after lysozyme treatment were analyzed. An arrow indicates the scFv protein. M=Mark12, molecular weight standard of Invitrogen.

The scFv gene was isolated via PCR using the primers 5-S(5'-aaa cat atg aaa tac cta ttg cct acg gc-3' (SEQ ID NO: 74)) and 3-S1 (5'-aaa aag ctt act acg agg aga cgg-3' (SEQ ID NO: 75)). The corresponding S1 protein contains a PelB signal sequence which is responsible for transport of the protein to the periplasm of E. coli. The PCR-fragment was cut with NdeI and HindIII and inserted into NdeI/HindIII-cut pBW22 to create plasmid pBW22-pelB-S1 containing the rhamnose inducible rhaBAD promoter (FIG. 10). The sequence of the S1 insert of plasmid pBW22-pelB-S1 was confirmed by sequencing. Strain W3110 (DSM 5911, Deutsche Sammlung von Mikroorganismen and Zellkulturen GmbH, Braunschweig, Germany) was transformed with plasmid pBW22-pelB-S1. The plasmids were isolated from different clones and verified by restriction analysis. E. coli W3110 (pBW22-pelB-S1) was tested for its capacity to produce soluble S1. Overnight cultures [in NYB medium (10 g/l tryptone, 5 g/l yeast extract, 5 g/l sodium chloride) supplemented with 100 µg/ml of Ampicillin, 37° C.] were diluted (1:50) in 20 ml of fresh glycerol medium [as described by Kortz et al., 1995, J. Biotechnol. 39, 59-65, with the exception of the vitamin solution (as described by Kulla et al., 1983, Arch. Microbiol, 135, 1)] and incubated at 30° C. Rhamnose (0.2%) was added when the cultures reached an $OD_{600}$ of about 0.4. Samples (1 ml) were taken at different time intervals, centrifuged and the pellets were stored at −20° C. The frozen cells were lysed according to the above described lysozyme treatment and the supernatants and insoluble protein pellets were analysed via SDS-PAGE (FIG. 11) and Bioanalyzer. Most of the S1 protein (mg/L/100$OD_{600}$) was produced in the soluble protein fraction.

Example 11

Figure 12:
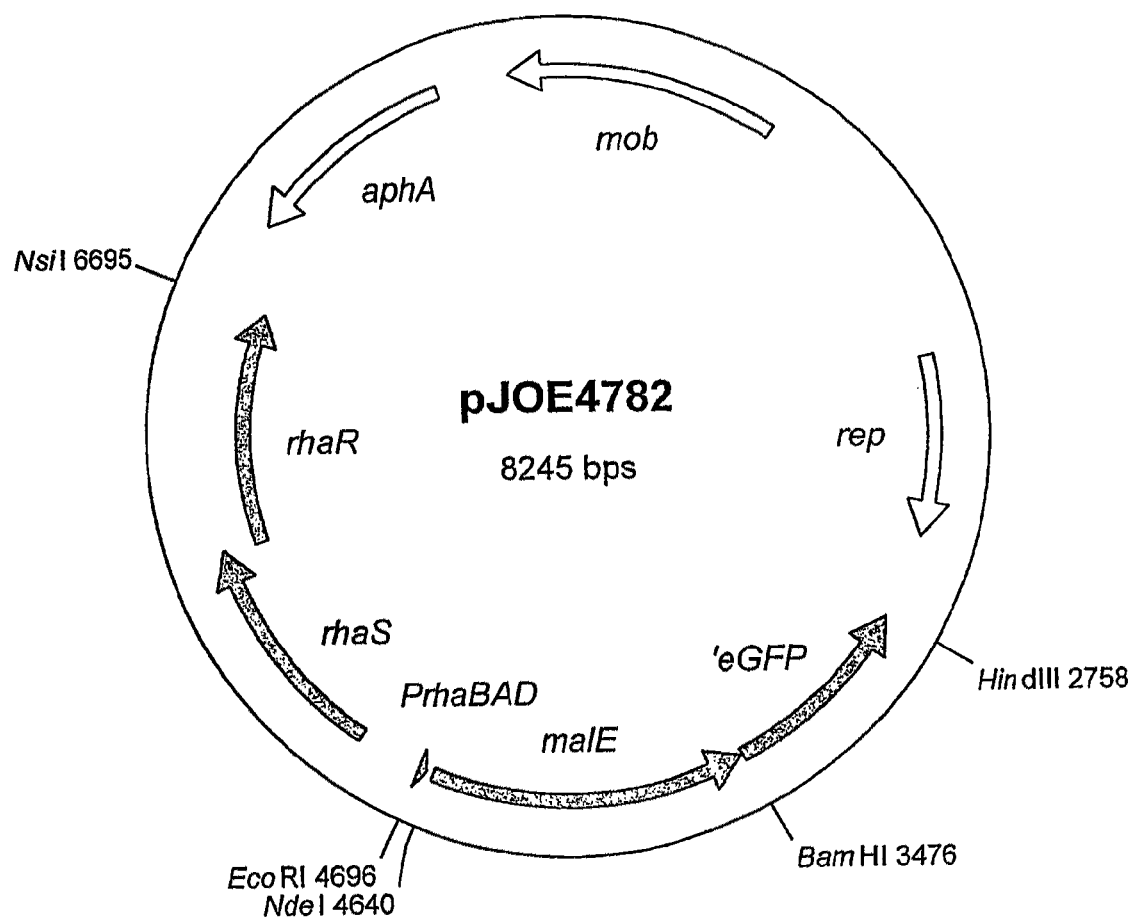
FIG. 12 shows the broad-host-range plasmid pJOE4782 comprising the L-rhamnose inducible rhaBAD promoter in combination with the genes of the regulatory proteins RhaS and RhaR of the L-rhamnose operon of *Escherichia coli*. Plasmid pJOE4782 further contains a sequence coding for a MalE signal peptide operably linked to a sequence coding for the GFP reporter protein.

Construction of a Broad-Host-Range Rhamnose Expression Plasmid for Pseudomonas and Related Bacteria The following cloning experiments were performed in Escherichia coli JM109. The broad-host-range cloning vector pBBR1MCS-2 (NCBI accession number U23751) was cut with AgeI/NsiI. The lacZα gene was deleted and replaced by the oligonucleotides 3802 (5'-tgt taa ctg cag gat cca agc tta-3') and 3803 (5'-ccg gta agc ttg gat cct gca gtt aac atg ca-3') to get plasmid pJOE4776.1. The rhaRSP fragment was provided by plasmid pJKS408 (unpublished) which contains the genomic rhaRS fragment (2 kb) of *Escherichia coli* JM109. Plasmid pJKS408 was cut with BamHI/HindIII and ligated to the BamHI/HindIII cut eGFP fragment (0.7 kb) of plasmid pTST101 [Stumpp, T., Wilms, B., Altenbuchner, J. (2000): Ein neues, L-Rhamnose-induzierbares Expressionssystem für *Escherichia coli*. Biospectrum 6, 33-36]. The rhaRSP-malE-eGFP fragment (4 kb) was isolated via NsiI/HindIII from the resulting plasmid pJOE4030.2 and integrated into NsiI/HindIII cut pJOE4776.1. Plasmid pJOE4776.1 (FIG. 12) contains the rhaBAD promoter region in combination with the genes of the regulatory proteins RhaS and RhaR of the rhamnose operon of *Escherichia coli* in a broad-host-range plasmid backbone.

Example 12

Rhamnose Induction of a Nitrilase in Shake Flasks

Figure 13:
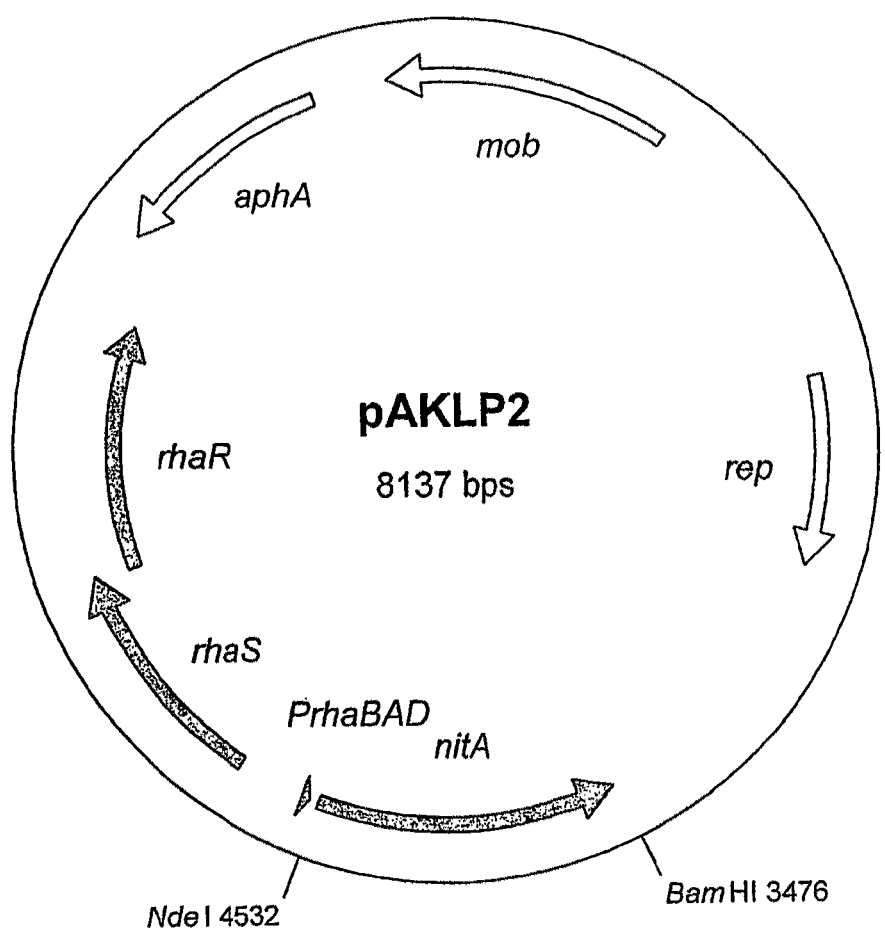
FIG. 13 shows plasmid pAKLP2 comprising the L-rhamnose inducible rhaBAD promoter and a sequence (nitA) coding for a Nitrilase protein.
Figure 14:
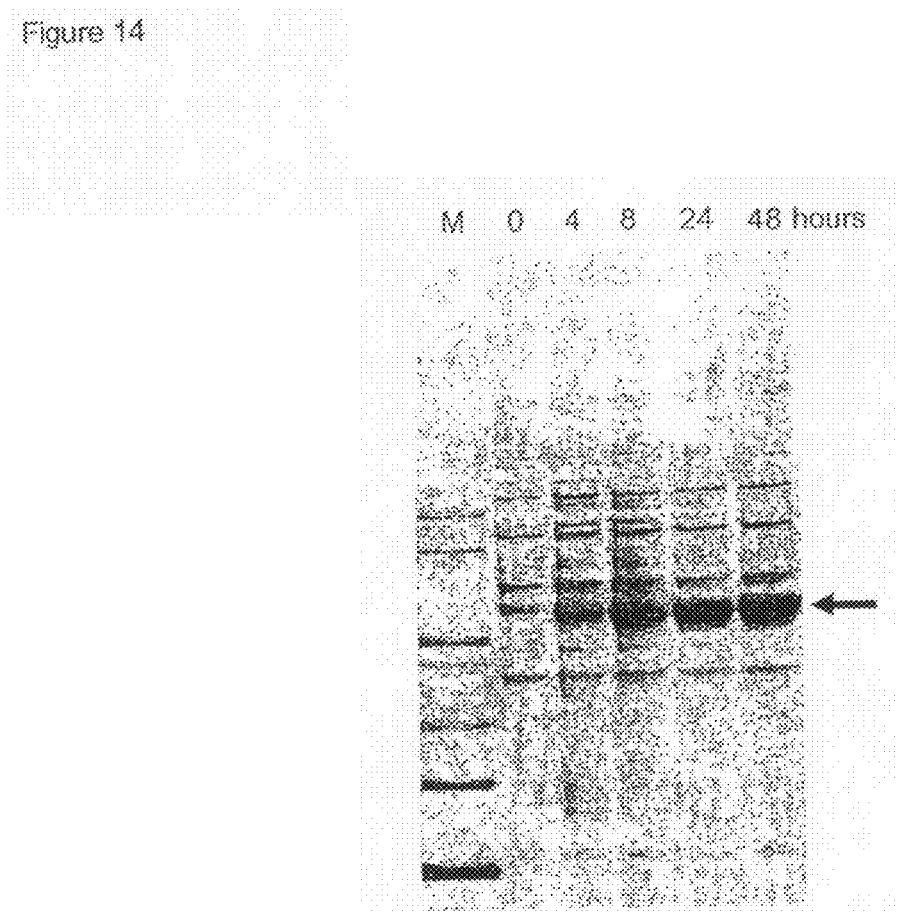
FIG. 14 shows SDS-PAGE of cells of the induced *Pseudomonas putida* strain KT2440 (pAKLP2). Samples were taken after different time intervals as indicated. An arrow indicates the Nitrilase protein. M=Mark12, molecular weight standard of Invitrogen.

The nitrilase gene was cut with NdeI and BamHI from Plasmid pDC12 (Kiziak et al., 2005) and inserted into NdeI/BamHI-cut pJOE4782.1 to create plasmid pAKLP2 containing the L-rhamnose inducible rhaBAD promoter (FIG. 13). *E. coli* XL1-Blue was transformed with plasmid pAKLP2 as an intermediate step. The plasmids were isolated from different clones and verified by restriction analysis. *Pseudomonas putida* KT-2440 (DSM 6125, Deutsche Sammlung von Mikroorganismen and Zellkulturen GmbH, Braunschweig, Germany) was transformed with the isolated plasmid pAKLP2 from *E. coli* XL1blue(pAKLP2). *Pseudomonas putida* KT-2440 (pAKLP2) was tested for its capacity to produce nitrilase. Overnight cultures [in NYB medium (10 g/l tryptone, 5 g/l yeast extract, 5 g/l sodium chloride) supplemented with 50 µg/ml of Kanamycin, 30° C.] were diluted in 20 ml of fresh glycerol medium [as described by Kortz et al., 1995, J. Biotechnol. 39, 59-65, with the exception of the vitamin solution (as described by Kulla et al., 1983, Arch. Microbiol, 135, 1)] to an $OD_{600}$ of about 0.1 and incubated at 30° C. L-rhamnose (1.0%) was added when the cultures reached an ($OD_{600}$ of about 0.25. Samples (1 ml) were taken at different time intervals, centrifuged and the pellets were stored at −20° C. The pellets were resuspended in Tris/HCl-buffer (50 mM, pH 8.0) and the cell suspensions were analysed via SDS-PAGE (FIG. 14).

Example 13

L-Rhamnose Induction of a Fragment Antibody (FabM) in Shake Flasks

Figure 15:
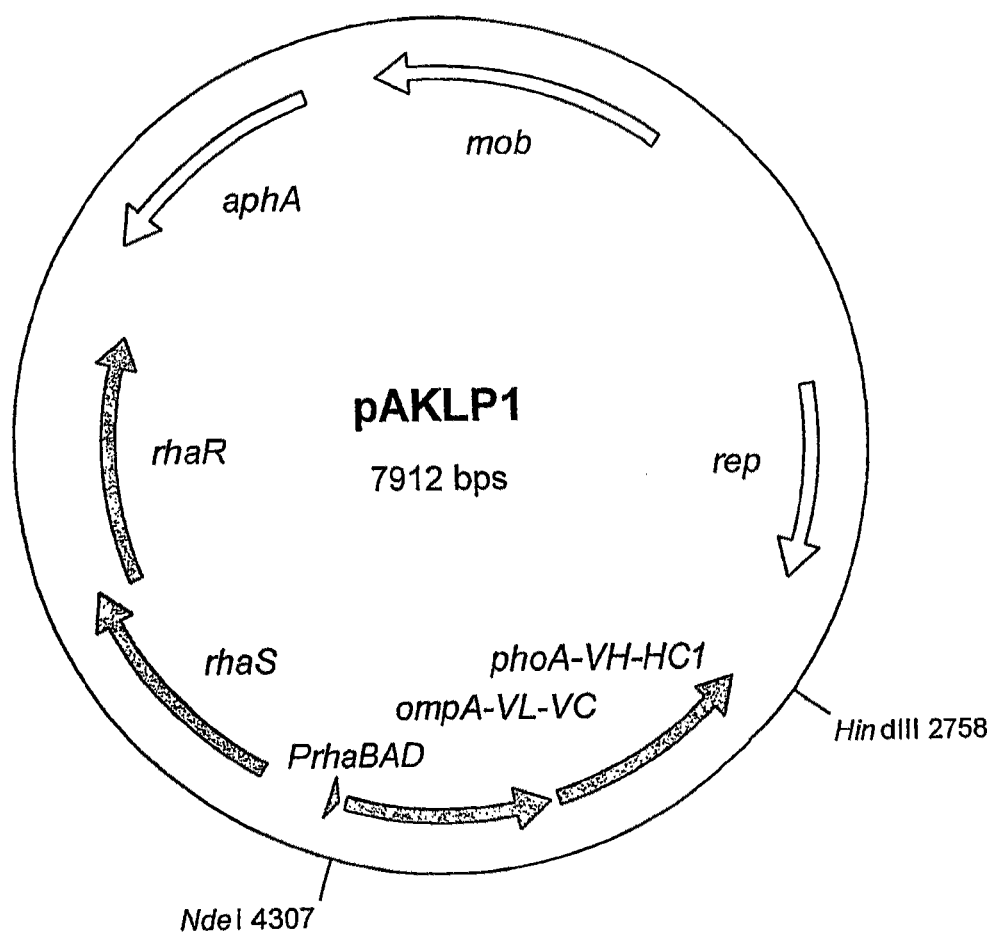
FIG. 15 shows plasmid pAKLP1 comprising the L-rhamnose inducible rhaBAD promoter and sequences coding for the Fab-M heavy and light chains which are operably linked to a sequence coding for the OmpA signal peptide and a sequence coding for the PhoA signal peptide, respectively.
Figure 16:
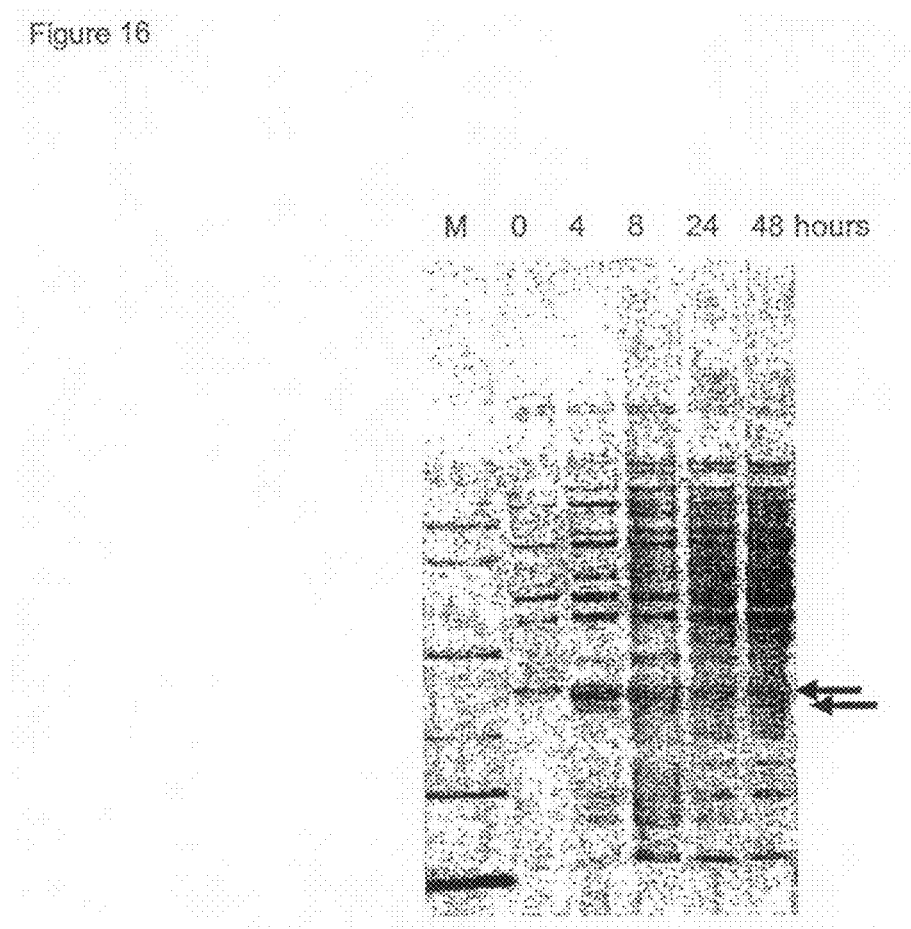
FIG. 16 shows SDS-PAGE of cells of the induced *Pseudomonas putida* strain KT2440 (pAKLP1). Samples were taken after different time intervals as indicated. The arrows indicate the FabM heavy and light chains. M=Mark12, molecular weight standard of Invitrogen.

The Fab-M gene was cut with NdeI and BamHI from plasmid pBW22-FabM and inserted into NdeI/BamHI-cut pJOE4782.1 to create plasmid pAKLP1 containing the L-rhamnose inducible rhaBAD promoter (FIG. 15). *E. coli* XL1-Blue was transformed with plasmid pAKLP1 as an intermediate step. The plasmids were isolated from different clones and verified by restriction analysis. *Pseudomonas putida* KT-2440 (DSM 6125, Deutsche Sammlung von Mikroorganismen und Zellkulturen GmbH, Braunschweig, Germany) was transformed with the isolated plasmid pAKLP1 from *E. coli* XL1blue (pAKLP1). *Pseudomonas putida* KT-2440 (pAKLP1) was tested for its capacity to produce Fab-M. Overnight cultures [in NYB medium (10 g/l tryptone, 5 g/l yeast extract, 5 g/l sodium chloride) supplemented with 50 µg/ml of Kanamycin, 30° C.] were diluted in 20 ml of fresh glycerol medium [as described by Kortz et al., 1995, J. Biotechnol. 39, 59-65, with the exception of the vitamin solution (as described by Kulla et al., 1983, Arch. Microbiol, 135, 1)] to an $OD_{600}$ of about 0.1 and incubated at 30° C. L-rhamnose (1.0%) was added when the cultures reached an ($OD_{600}$ of about 0.25. Samples (1 ml) were taken at different time intervals, centrifuged and the pellets were stored at −20° C. The pellets were resuspended in Tris/HCl-buffer (50 mM, pH 8.0) and the cell suspensions were analysed via SDS-PAGE (FIG. 16).

Example 14

Single Chain Antibody Expression Using an *Escherichia coli* Secretion System in High Cell Density Fermentation

Figure 17:
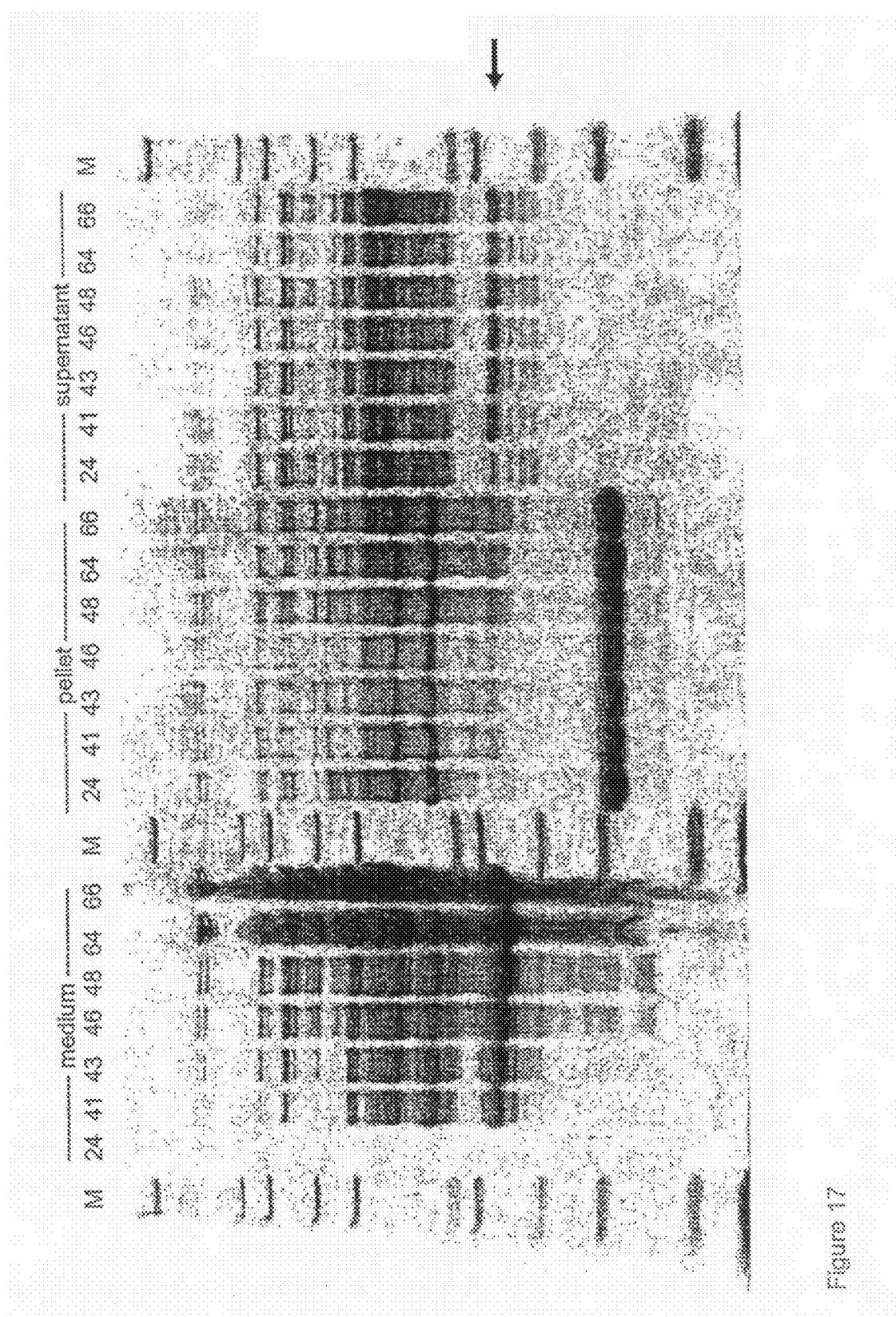
FIG. 17 shows SDS-PAGE of fermentation samples of the *Escherichia coli* strain W3110 (pBW22-pelB-S1). Samples were taken after different time intervals (in hours) as indicated. An arrow indicates the scFv protein. M=Mark12, molecular weight standard of Invitrogen.

*Escherichia coli* W3110 was transformed with plasmid pBW22-pelB-S1. The plasmids were isolated from different clones and verified by restriction analysis and one clone was used for further experiments. Pre-cultures in shake flask were inoculated from single colonies in Lonza's batch phase medium. The pre-culture was used to inoculate a 20 L fermenter. Cells were grown according to Lonza's high cell density fermentation regime. Samples (10 ml) of the culture were taken at different time points before and after rhamnose induction. Cells were separated from fermentation medium by centrifugation at 10'000 g. SDS gel analysis of samples from the cell free fermentation medium show a protein band at 28.4 kD with increasing density. This protein is the single chain antibody S1 released from the growing culture into the fermentation medium. A quantification of the S1 protein content with an Agilent 2100 Bioanalyser (Agilent, Palo Alto, USA) indicated an accumulation of up to 2 g/L/100 $OD_{600}$ S1 protein in the fermentation broth after rhamnose induction. After lysozyme treatment of the cell pellet, the insoluble protein pellet contained only traces of the S1 protein whereas the soluble protein fraction (supernatant) showed a strong S1 protein band, corresponding to about 1 g/L/100 $OD_{600}$ (see FIG. 17).

The invention claimed is:

1. A vector for the expression of Fab fragments comprising the rhaBAD promoter region of the L-rhamnose operon operably linked to a transcriptional unit comprising:
   a) a nucleic acid sequence encoding a Fab fragment,
   b) a prokaryotic signal sequence operably linked to said nucleic acid sequence, wherein said prokaryotic signal sequence is selected from signal peptides of the periplasmic binding proteins LamB and MalE, wherein the expression of said nucleic acid sequence is controlled by said promoter region, and
   c) a translation initiation region upstream of the initiation point of the translation of said transcriptional unit, said translation initiation region consisting of the sequence AGGAGATATACAT (SEQ ID NO. 2), wherein said translation initiation region is operably linked to said nucleic acid sequence.

2. The vector of claim 1, wherein said rhaBAD promoter consists of sequence SEQ ID NO. 1 or a sequence complementary thereof.

3. The vector of claim 1, wherein said transcriptional unit further comprises a transcription termination region which is rrnB transcriptional terminator sequence.

4. The vector of claim 3, wherein heavy and light chains of said Fab fragment are encoded by a dicistronic transcriptional unit, whereas each chain is operably linked to said prokaryotic signal sequence and an identical translation initiation region upstream of the initiation point of the translation of said transcriptional unit.

5. The vector of claim 4, wherein said rhaBAD promoter region and said operably linked transcriptional unit consists of sequence SEQ ID NO. 3 or a sequence complementary thereof.

6. A method for producing a Fab fragment in *E. coli* comprising the steps of:
   a) constructing a vector of claim 1,
   b) transforming *E. coli* with said vector,
   c) allowing expression of said Fab fragment in a cell culture system under suitable conditions, and
   d) recovering said Fab fragment from the cell culture system.

7. The method of claim 6, wherein heavy and light chains of the Fab fragment are expressed in said cell culture system in equal amounts.

8. The method of claim 6, wherein expression of said polypeptide is carried out in glycerol containing medium.

9. An isolated and purified nucleic acid sequence operably linked to a transcriptional unit comprising:
   a) a nucleic acid sequence encoding a Fab fragment,
   b) a prokaryotic signal sequence operably linked to said nucleic acid sequence, wherein said prokaryotic signal sequence is selected from signal peptides of the periplasmic binding proteins LamB and MalE, wherein the expression of said nucleic acid sequence is controlled by rhaBAD promoter region of the L-rhamnose operon, and
   c) a translation initiation region upstream of the initiation point of the translation of said transcriptional unit, said translation initiation region consisting of the sequence AGGAGATATACAT (SEQ ID NO. 2), wherein said translation initiation region is operably linked to said nucleic acid sequence.

10. The isolated and purified nucleic acid sequence of claim 9, wherein said rhaBAD promoter consists of the sequence SEQ ID NO. 1 or a sequence complementary thereof.

11. The isolated and purified nucleic acid sequence of claim 10, wherein said rhaBAD promoter region and said operably linked transcriptional unit consists of the sequence SEQ ID NO. 3 or a sequence complementary thereof.

* * * * *